United States Patent [19]

Kilbourn et al.

[11] Patent Number: 5,028,627

[45] Date of Patent: Jul. 2, 1991

[54] METHOD OF USING ARGININE DERIVATIVES TO INHIBIT SYSTEMIC HYPOTENSION ASSOCIATED WITH NITRIC OXIDE PRODUCTION OR ENDOTHELIAL DERIVED RELAXING FACTOR

[75] Inventors: Robert G. Kilbourn, Houston, Tex.; Steven Gross, New York, N.Y.; Roberto Levi, New York, N.Y.; Owen W. Griffith, New York, N.Y.

[73] Assignees: Cornell Research Foundation, Inc., Ithaca, N.Y.; Board of Regents, The University of Texas System, Austin, Tex.

[21] Appl. No.: 406,909

[22] Filed: Sep. 13, 1989

[51] Int. Cl.$^5$ .................... A61K 31/195; A61K 45/5; A61K 37/66; A61K 37/10

[52] U.S. Cl. ...................................... 514/565; 514/12; 514/930; 424/85.2; 424/85.5; 424/85.1

[58] Field of Search ...................... 514/565, 930, 12; 424/85.2, 85.5, 85.1

[56] References Cited

U.S. PATENT DOCUMENTS 4,282,217  8/1981  Baglioni et al. .

OTHER PUBLICATIONS

Palmer, R. M. J. et al. (Jun. 30, 1988) L-Arginine is the Physiological Precursor for the Formation of NO in EDR. Biochem. Biophis Res. Commun 153(3) 1251-1256.

Stuehr, D. J. et al. (1987) Induction of $NO_2/NO_3$ Synthesis in Murine Macrophages by BCG Infection, Lymphokines or Interferony J. Immonol 139:518-525.

Schmidt, H. H. H. W. et al. (1988) Arginine is a Physiological Precursor of Endotherlium Derived NO Eur. J. Pharmacol. 154:213-216.

Stuehr, D. J. et al., J. Exp. Med. vol. 169 (1989), 1011-1020.

Aisaka, K. et al., Biochem. Biophys. Res. Commun., vol. 160 (1989) 881-886.

Rees, D. D. et al., Proc. Natl. Acad. Sci. U.S.A., vol. 86 (1989) 3375-3378.

Iyengar, R. et al., Proc. Natl. Acad. Sci. U.S.A., vol. 84, (1987), 6369-6373.

Palmer, R. M. J. et al., Nature, vol. 333 (1988) 664-666.

Stuehr, D. J. et al., Biochem. Biophys. Res. Commun., vol. 161 (1989) 420-426.

Turan, A. et al., Acta Chimica Academiae Scientiarum Hungaricae, Tomas 85 (1975) 327-332.

Primary Examiner—Glennon H. Hollrah
Assistant Examiner—Gary E. Hollinden
Attorney, Agent, or Firm—Arnold, White & Durkee

[57] ABSTRACT

A method for prophylaxis of treatment of an animal for systemic hypotension induced by internal nitrogen oxide production. The method involves administering a therapeutically effective amount of certain arginine derivatives to inhibit nitrogen oxide formation from arginine. Preferaby $N^G$-substituted arginine or an $N^G,N^G$-disubstituted arginine (having at least one hydrogen on a terminal guanidino amino group replaced by another atomic species) is administered to an animal possibly developing or already having induced systemic hypotension. The arginine derivatives are preferably of the L configuration and include pharmaceutically acceptable addition salts. Prophylaxis or treatment or systemic hypotension in a patient which has been induced by chemotherapeutic treatment with biologic response modifiers such as tumor necrosis factor or interleukin-2 may be accomplished. Treatment of an animal for systemic hypotension induced by endotoxin, i.e., septic shock may also be accomplished by treatment with the arginine derivatives.

43 Claims, 15 Drawing Sheets

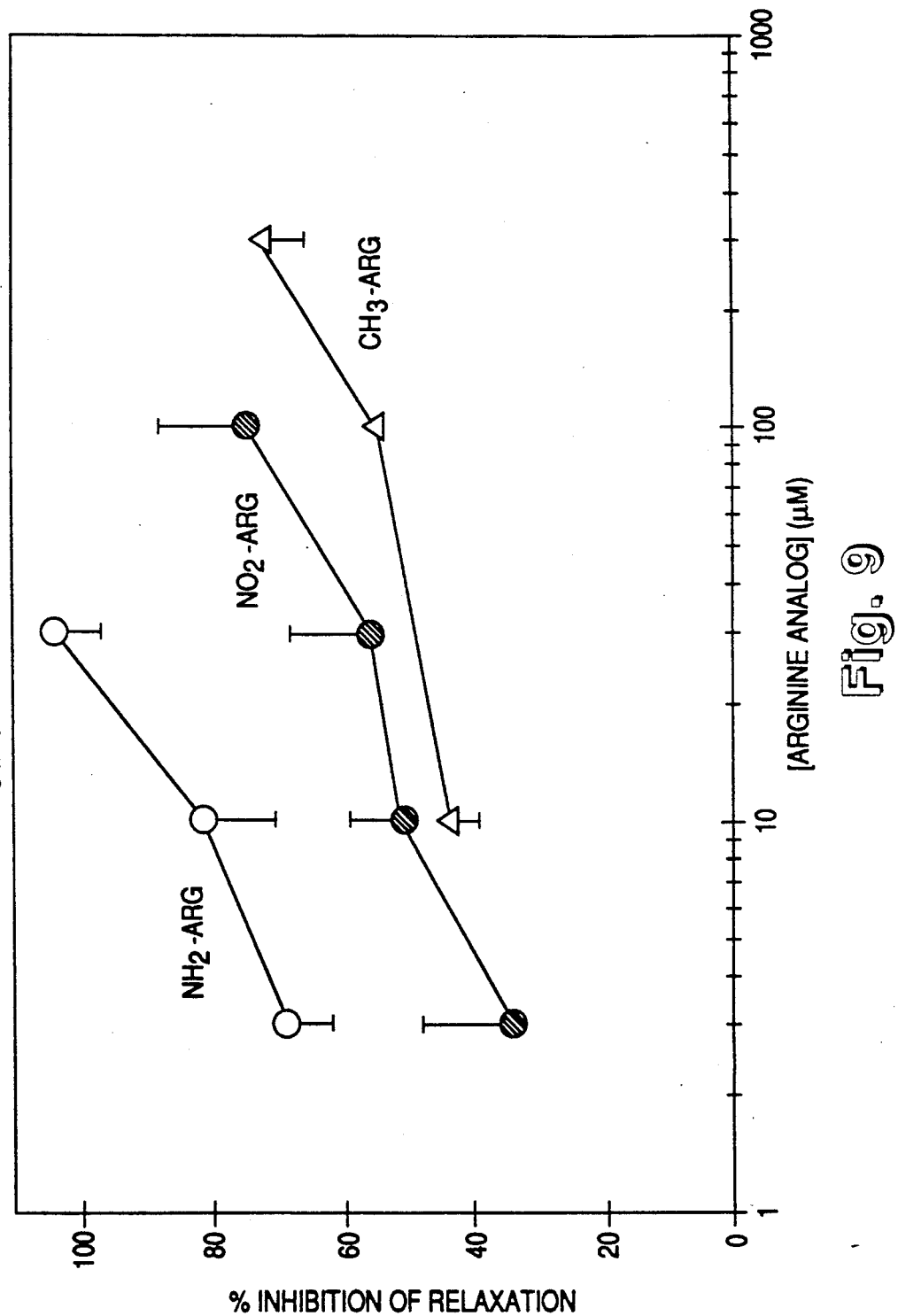

METHOD OF USING ARGININE DERIVATIVES TO INHIBIT SYSTEMIC HYPOTENSION ASSOCIATED WITH NITRIC OXIDE PRODUCTION OR ENDOTHELIAL DERIVED RELAXING FACTOR

Certain research relating to the development of this invention was supported by the United States Public Health Service grants which may give the United States government certain rights in the present invention.

This application relates to a patent application filed on the same date (Sept. 13, 1989) entitled "Isolating Aminoarginine and Use to Block Nitric Oxide Formation in Body" by Owen W. Griffith, having an inventor and assignee in common and incorporated by reference herein.

BACKGROUND OF THE INVENTION

The present invention relates to the prophylaxis and alleviation of hypotension induced by nitrogen oxide production.

In 1980, Furchgott and Zawadski (Nature 288: 373-376) demonstrated that endothelial cells, which line blood vessels, can be stimulated to release a substance which relaxes vascular smooth muscle i.e., causes vasodilatation. Since the chemical nature of this substance was completely unknown, it was simply named endothelium-derived relaxing factor (DRF). It is now widely accepted that many naturally-occuring substances which act as physiological vasodilators mediate all or part of their action by stimulating release of EDRF; these substances include, acetylcholine, histamine, bradykinin, leukotrienes, ADP, ATF, substance P, serotonin, thrombin and others. Although the extremely short lifetime of EDRF (several seconds) hampered efforts to chemically identify this molecule, in 1987 several laboratories suggested that EDRF may be nitric oxide (NO), which spontaneously decomposes to nitrate and nitrite. A fundamental problem in accepting this NO hypothesis was that mammalian systems were not known to contain an enzymatic pathway which could synthesize NO, additionally, a likely precursor for NO biosynthesis was unknown. After observing that the arginine analog L-$N^G$-methylarginine (L-NMA) could inhibit vascular EDRF/NO synthesis induced by acetylcholine and histamine, and that EDRF/NO synthesis could be restored by adding excess L-arginine, certain of the present inventors proposed that arginine is the physiological precursor of EDRF/NO biosynthesis (Sakuma et al., PNAS 85: 8664-8667, 1988). Additional evidence supporting this proposal was reported almost simultaneously. Certain of the present inventors later demonstrated that inhibition of EDRF/NO synthesis in the anesthetized guinea pig raises blood pressure, suggesting that EDRF/NO is an important physiological regulator of blood pressure (Aisaka et al., BBRC 160: 881-886, 1989).

Other laboratories had demonstrated that macrophage cells become "activated" by 12-36 hour treatment with gamma-interferon, bacterial endotoxin and various cytokines. This "activation" is associated with initiation of tumor cell killing and generation of nitrite and nitrate from L-arginine. We observed that activated macrophage actually make NO from L-arginine (just like endothelial cells) and that this NO subsequently reacts with oxygen to form more oxidized nitrogen metabolites which appear to be physiologically inert (Stuehr et al., J. Exp. Med. 169: 1011-1020, 1989). The enzyme responsible for NO synthesis (nitric oxide synthetase) has been partially characterized by some of the present inventors (Stuehr et al. BBRC161: 420-426, 1989) and acts to oxidize the terminal amino group of arginine, resulting in production of NO and citrulline. It is now believed that macrophage-derived NO is an important tumoricidal and bactericidal agent. Since bacterial endotoxin, gamma-interferon and other cytokines can trigger NO generation by macrophage cells it appeared that: 1) endothelial cell NO generation may be stimulated by similar stimuli and 2) septic shock (i.e., systemic vasodilatation induced by bacterial endotoxin) may result from massive activation of NO biosynthesis. Speculation that the latter hypothesis was correct was fueled by a prior report that urinary nitrate levels are grossly elevated by treatment of rats with bacterial endotoxin (Wagner et al., PNAS 80: 4518-4521, 1983).

Cytokines are well known to cause morphological and functional alterations in endothelial cells described as "endothelial cell activation". Distinct immune-mediators such as tumor necrosis Factor (TNF), interleukin-1 (IL-1), and gamma-interferon (IFN) appear to induce different but partially overlapping patterns of endothelial cell activation including increased procoagulant activity (Bevilaqua, 1986), PGI2 production (Rossi, 1985 Science 229,174), HLA antigen expression (Pober 1987) and lymphocyte adhesion molecules (Harlan 1985; Cavender 1987). Although these cytokines are reported to cause hypotension, vascular hemorrhage, and ischemia, the underlying mechanisms of altered vasoactivity is unclear (Goldblum et al. 1989; Tracey et al. Science 234:470, 1986). A potential mediator of altered vasoactivity is endothelial-derived relaxing factor (EDRF).

In both clinical and animal (Dvorak, 1959) studies on the effects of biological response modifiers a major dose limiting toxicity has been hypotension and vascular leakage.

SUMMARY OF THE INVENTION

The present invention involves a method for prophylaxis or treatment of an animal for systemic hypotension induced by a biological response modifier. Said method involves administering, preferably intravascularly, a therapeutically effective amount of an inhibitor of nitrogen oxide formation from arginine. Although preferable administration is intravascular, it is contemplated that other parenteral administration routes such as peritoneal, intramuscular or subdermal injectioin, for example, may prove useful. Enteral or topical administration may also prove beneficial for certain clinical conditions.

In one embodiment the inhibitor is $N^G$-substituted arginine or an $N^G,N^G$-disubstituted arginine which is administered to an animal possibly developing or having such induced systemic hypotension. The arginine antagonists of the present invention are preferably of the L configuration and include any pharmaceutically acceptable addition salts as commensurate with planned treatments.

Biological response modifiers which may induce such hypotension include gamma-interferon, tumor necrosis factor, interleukin-1 or interleukin-2. A particular use of the method of the present invention is for prophylaxis or treatment of systemic hypotension in a patient induced by chemotherapeutic treatment with at least one of tumor necrosis factor and interleukin-2. In this aspect the method involves intravascularly administering to subject of such chemotherapy a therapeutically effective amount of $N^G$-substituted arginine or an $N^G,N^G$-disubstituted arginine to a patient.

An important aspect of the present invention is as a method for treatment of an animal for systemic hypotension induced by endotoxin, i.e., septic shock. Although prophylaxis is inappropriate here, treatment is essential, the treatment involving intravascularly administering to such a hypotensive animal a therapeutically effective amount of an arginine antagonist such as $N^G$-substituted arginine or $N^G,N^G$-disubstituted arginine.

Preferred $N^G$-substituted arginine antagonists of the L configuration for uses as described herein include $N^G$-aminoarginine, $N^G$-nitroarginine, and $N^G$-alkyl arginines such as $N^G$-methylarginine, $N^G$-ethylarginine, NG-propylarginine or $N^G$-butylarginine. Therapeutically effective amounts of the substituted or disubstituted arginine antagonists inhibit production in the animal or patient of nitrogen oxide from arginine, thus obviating the hypotensive effects of nitrogen oxide.

In a more general sense, the present invention may relate to a method for prophylaxis or treatment of an animal for systemic hypotension related to induced production of nitrogen oxide. Said method would involve intravascularly administering a therapeutically effective amount of an arginine antagonist inhibiting production of nitrogen oxide from arginine, to an animal possibly developing or having systemic hypotension. Effective arginine antagonists may include a wide variety of compounds, particularly arginine derivatives which inhibit nitric oxide production. Many substituents, for example, on the guanidino group of arginine or analogous citrulline functional groups should function as well. The hypotension-producing nitrogen oxide may be directly or indirectly induced by at least one of gamma-interferon, tumor necrosis factor, interleukin-1, interleukin-2, and endotoxin. In a preferred aspect, the arginine antagonists usable as described herein include $N^G$-substituted arginine or $N^G$,NG-disubstituted arginine. These antagonists preferably have alkyl substituents selected from the group consisting of methyl, ethyl, propyl and butyl. Analogous antagonists may include derivatized alkyl substituents selected from the group consisting of hydroxyalkyl, carboxyalkyl and aminoalkyl. The arginine antagonists usable in the practice of the present invention comprising arginine with at least one $N^G$ substituent selected from the group consisting of alkyl, hydroxyalkyl, alkenyl, hydroxyalkenyl, and monosaccharide. The therapeutically effective amount of arginine antagonists of the present invention is an amount sufficient to inhibit production of nitrogen oxide from arginine. The nitrogen oxide thought to be most directly the product of arginine is nitric oxide, which rapidly degrades to nitrate and nitrite ions in the presence of oxygen.

When intravascularly administering a canine with a therapeutically effective amount of $N^G$-methylarginine, the therapeutically effective amount is between about 4 mg/kg and about 100 mg/kg. The appropriate dose for a human and/or for other arginine antagonists should be between about 0.1 mg/kg and about 100 mg/kg.

BRIEF DESCRIPTION OF THE DRAWINGS

FIG. 9 shows artery ring acetylcholine induced relaxation dose-response inhibition curves for certain $N^G$ substituted arginine derivatives.

DESCRIPTION OF THE PREFERRED EMBODIMENTS

Figure 1:
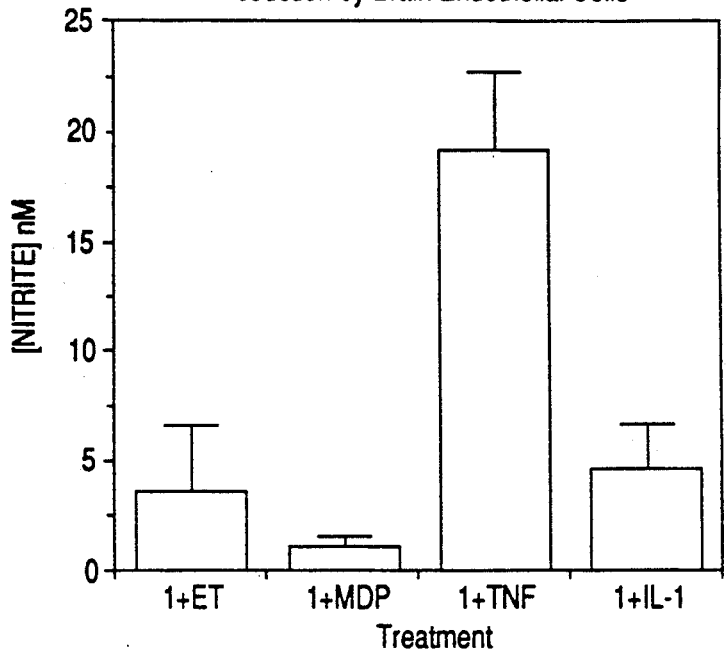
FIG. 1 shows the effects of gamma-interferon (IFN) in combination with various cytokines on the production of nitrites by brain endothelial cells (MBEC).

Clinical studies of biologic response modifiers have shown that a major dose limiting toxicity is hypotension. These cytokines have also been found to activate macrophages, a process that renders macrophages cytotoxic for tumor cells. Recent studies have implicated macrophage-derived nitric oxide, as the effector molecule responsible for tumor cell cytotoxicity. Nitric oxide is a highly reactive compound which spontaneously decomposes to nitrates and nitrites in the culture medium. Nitric oxide has also been demonstrated to be produced by vascular endothelial cells, previously being known as endothelial-derived relaxing factor (EDRF). EDRF has been found to cause relaxation of the smooth muscle of arteries in response to the infusion of hypotensive agents such as bradykinin or acetylcholine.

The present invention involves a finding that gamma interferon (100 U/ml) in combination with either tumor necrosis factor 500 U/ml), interleukin-1 (10 U/ml), or endotoxin 1 ug/ml.), can induce murine endothelial cells to accumulate nitrate in the culture medium (15 to 80 uM in 48 hours). These levels are comparable to those produced by activated macrophages. Tumor necrosis factor, interleukin-1 or endotoxin alone induced the production of minimal levels of nitrites (1–3 uM).

The release of vasoactive factors, such as nitric oxide, by endothelial cells may play a role in the development of hypotension associated with the administration these agents, in vivo. This invention relates to a demonstration that cultured murine brain endothelial cells produce NO in response to various combinations of cytokines and its potential role in the pathogenesis of vascular endothelial cell injury.

These examples are presented to describe preferred embodiments and utilities of the present invention and are not meant to limit the present invention unless otherwise stated in the claims appended hereto.

EXAMPLE 1

Materials—Recombinant murine gamma interferon, interleukin-1, and tumor necrosis factor (Genzyme). N-monomethyl-arginine was a gift from Dr. Moncada, London, England. Endotoxin (E.coli B126) and all other reagents (Sigma).

Endothelial cells—MBE cells were isolated from murine brain microvessels and cultured on gelatin-coated tissue culture dishes in DME/F12 media supplemented with 2% PPPHS, 5% FBS (Hyolone), 50 ug/ml ECGF (Biomed Tech), and 10 U/ml heparin (Sigma) as previously described (Belloni et al. 1989). The endothelial derivation of MBE cells was determined by the presence of a non-thrombogenic surface to platelets and immunofluorescent staining for Factor VIII related antigen. MBE cells were used between passage 6–9 for all experiments.

Nitrite Assay—MBE cells were cultured on gelatin-coated well plates (Corning) in 100 ul of culture medium and treated with cytokines at 3 days post-confluence. After 48 hours, nitrite production was determined by a colorimetric assay. Briefly, 50 ul of media was removed from each culture well and mixed with 50 ul of Greiss reagent (1% sulfanilamide and 0.1% naphthyethylene diamine dihydrochloride in 2% $H_3PO_4$, incubated for 10 minutes with shaking at 25 0, and the absorbance (OD) was measured in a microplate reader (Molecular Devices Corp.) and concentrations determined by comparison to a standard solution of $NaNO_2$ in water. Background nitrite levels in control cultures not receiving cytokines were subtracted from the experimental values. In certain experiments N-monomethyl arginine (NMA) was added to the growth medium at the time of cytokine addition, while in others arginine-free media was supplemented for the growth medium. All treatments were performed in triplicate and data presented as the mean value±standard deviation.

Effect of Cytokines on Nitrite Production by MBEC

Figure 2A:
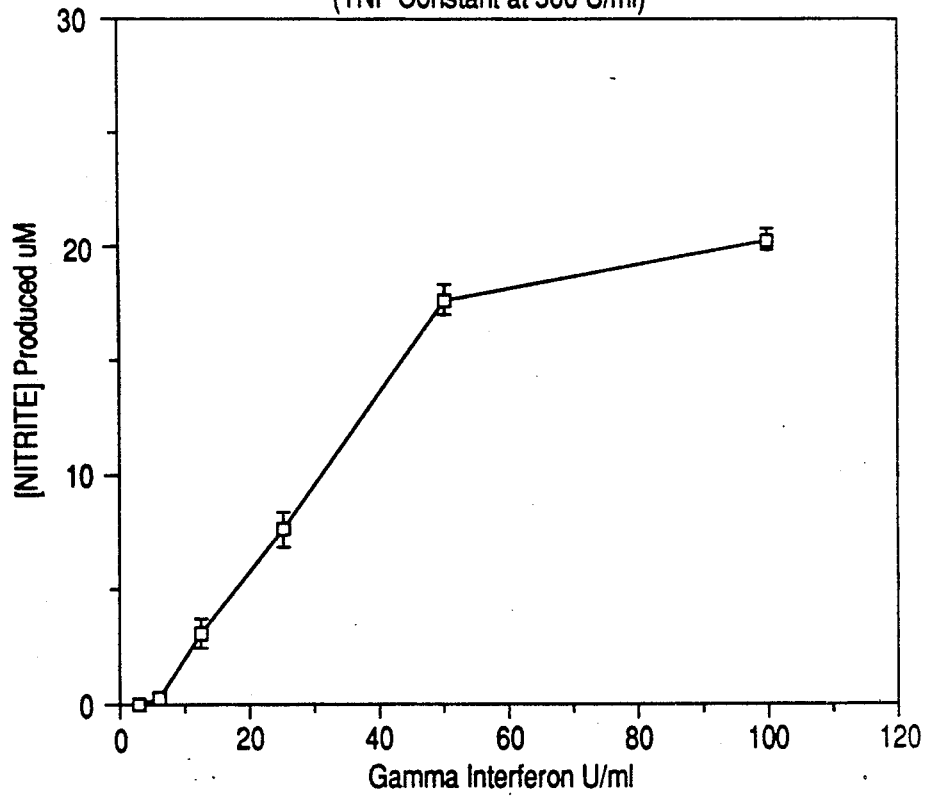
FIG. 2a shows nitrite produced by MBEC at constant tumor necrosis factor (TNF) concentration and a range of INF concentrations.
Figure 2B:
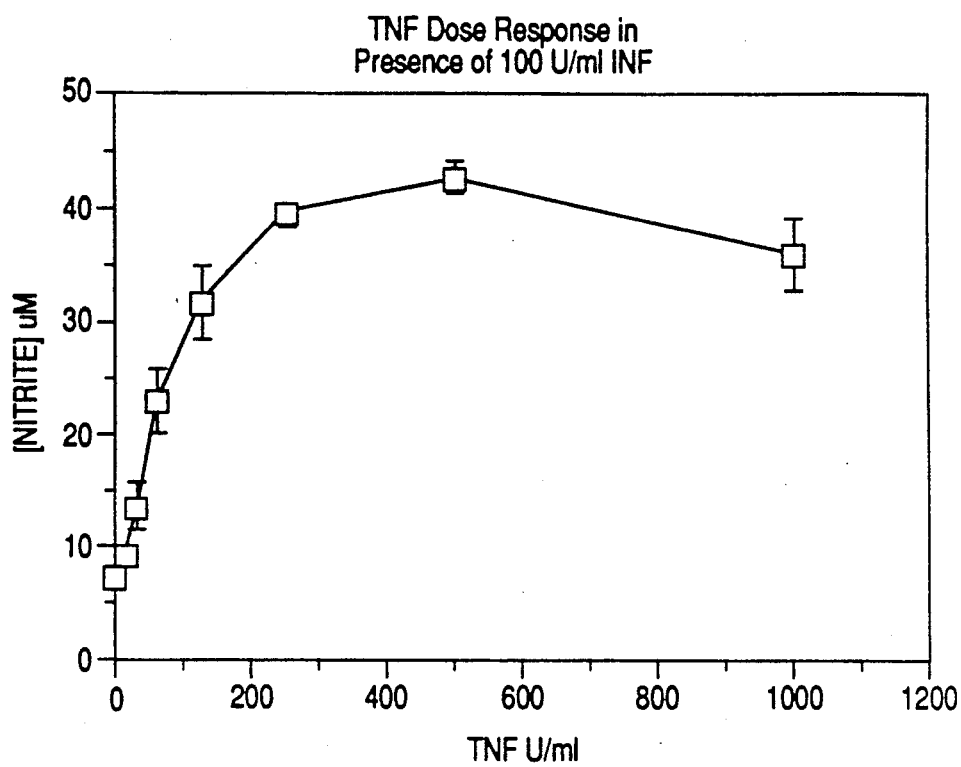
FIG. 2b shown nitrite produced by MBEC at constant INF concentration and a range of TNF concentrations.

The effects of IFN in combination with various cytokines on the production of nitrites by MBEC are illustrated in FIG. 1. Exposure of endothelial cells to IFN (100 U/ml) alone had no effect on nitrite production, however combinations of TNF (500 U/ml), Il-1 (10 U/ml) or endotoxinin (1 ug/ml) resulted in a synergistic effect on nitrite production compared with the effects of these three agents alone. Neither muramyl dipeptide (MDP) or Il-2 (data not shown) alone or in combination with gamma interferon effected nitrite production by MBEC. This lack of response distinguishes the MBE cells from activated macrophages which produce significant amounts of nitrites after exposure to MDP and IFN (Drapier et al. 1988). Gamma interferon and TNF was the most effective cytokine combination found to induce nitrite production (19.5 mM±5). Dose response curves for TNF and IFN are shown in FIGS. 2a and 2b. The accumulation of nitrites was proportional to the concentration of TNF added when gamma interferon was present at a concentration of 100 U/ml (FIG. 2b).

Figure 3:
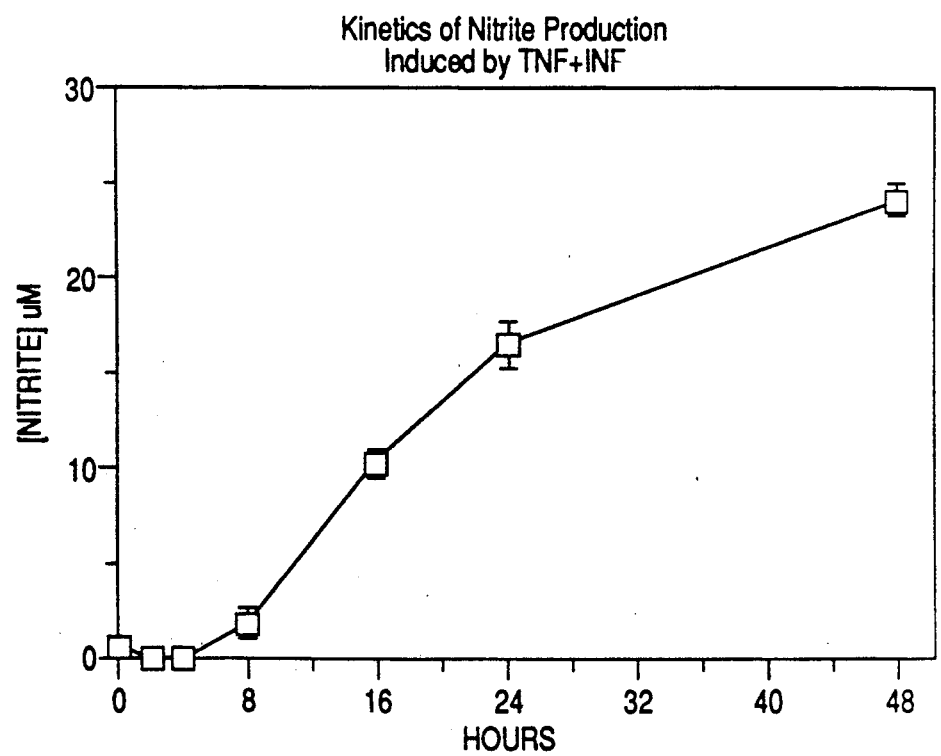
FIG. 3 shown MBEC nitrite production induced by TNF and INF as a function of time.

The accumulation of nitrites in the culture medium was also found to occur in a time dependent manner with the first detectable increase at 8 hours after addition of TNF and IFN (FIG. 3). The maximum accumulation was observed at 48 hours and therefore, in all subsequent studies nitrite measurements were performed 48 hours after the addition of TNF (500 U/ml) and IFN (100 U/ml). Although both TNF and IFN have been reported to cause morphological alterations in human umbilical cord endothelial cells no changes in the gross morphology of these murine microvascular endothelial cells was detected under these conditions.

Arginine is Required for Production of Nitrites

Figure 4:
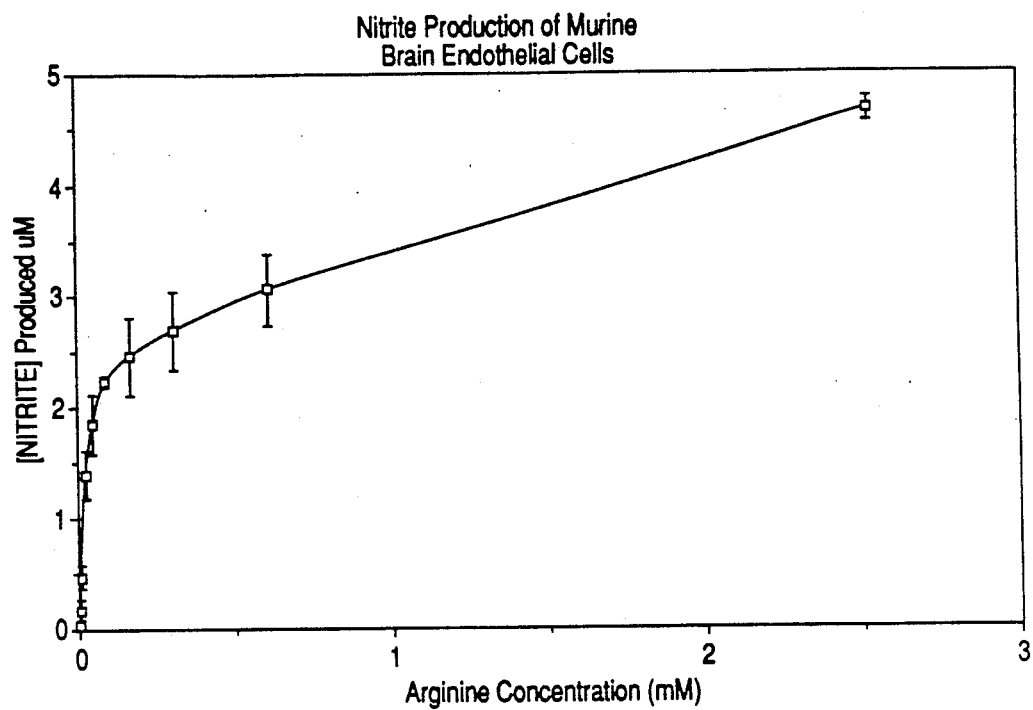
FIG. 4 shown nitrite produced by MBEC exposed to TNF and INF as a function of arginine concentration.
Figure 5:
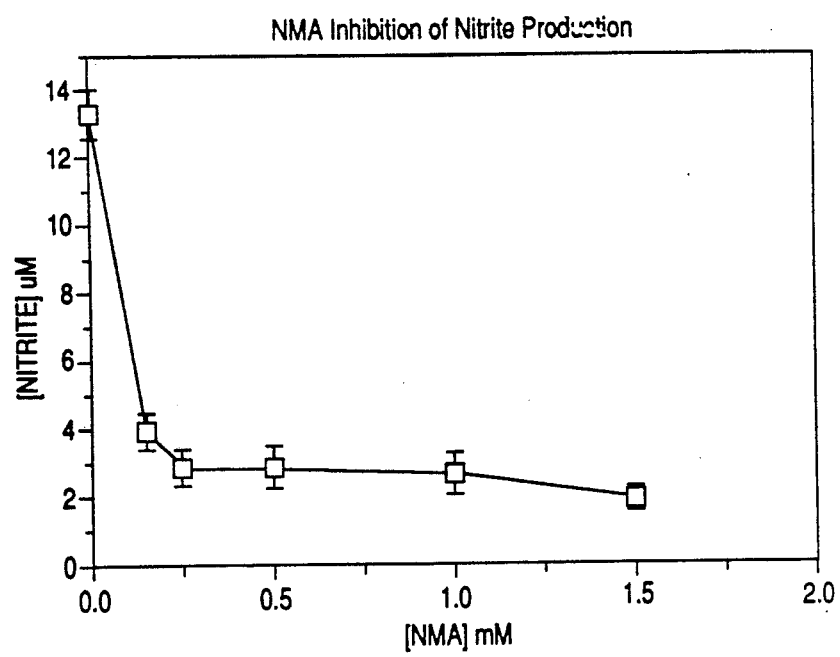
FIG. 5 shows inhibition by $N^G$methyl L-arginine (NMA) TNF and INF-induced nitrite production by MBEC.

The production of nitrites by MBE cells exposed to TNF and IFN did not occur in arginine-free culture medium, and increased in a dose dependent manner upon addition of L-arginine back to the medium (FIG. 4). Nitrite production was also inhibited by addition of the arginine derivative NMA (FIG. 5). This inhibition was proportional to the concentration of NMA and was maximal in the presence of 1 mM NMA. In addition, the inhibitory effect of NMA could be reversed by the addition of excess L-arginine, with 8 mM L-arginine completely reversing the effects of 1 mM NMA. These results suggest that microvascular endothelial cells produce nitric oxide in response to specific cytokines by de novo synthesis utilizing L-arginine as the physiological precursor. A similar metabolic pathway has been identified for the production of NO by large vessel endothelial cells in response to such hypotensive agents as bradykinin and acetylcholine (Palmer et al. 1988 BBRC 153:1251-1256; Kelm et al. 1988), suggesting that the hypotensive effects associated with administration of various cytokines in vivo may be mediated through the release of NO.

Figure 6:
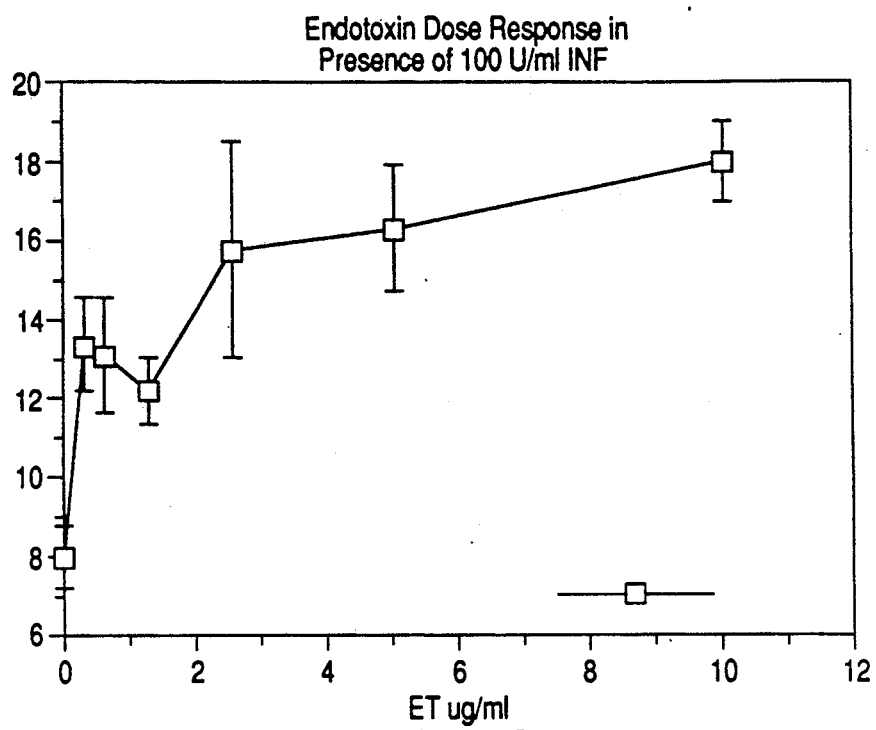
FIG. 6 shown nitrite produced by MBEC with INF as a function of endotoxin concentration.

As shown in FIG. 6, endotoxin showed a dose-dependent stimulation of nitrite production with MBEC in the presence of 100 units INF/ml.

EXAMPLE 2

Hypotension associated with the administration of tumor necrosis factor in the dog can be blocked by subsequent administration of $N^G$-monomethylarginine, for example. Furthermore, this inhibition of hypotension can be reversed by administration of an excess of arginine. These results show that nitric oxide is the mediator of hypotension induced by tumor necrosis factor. Furthermore, activation of nitric oxide synthesis may be involved in the pathogenesis of septic shock.

Reagents

Recombinant human tumor necrosis factor, specific activity $2 \times 10^7$ units/mg, was from the Niposn Chemical Corporation, Tokyo, Japan. Tumor necrosis factor was administered at a dose of 10 mcg/kg in a volume of 10 ml of phosphate buffered saline containing 2 mgs/ml of dog albumin. $N^G$-monomethylarginine was synthesized by adaptation of the method of Corbin and Reporter (Anal. Biochem. 57: 310–312, 1974) and was dissolved in 5 ml of phosphate buffered saline for administration at a dose of 15 mgs/kg. Arginine was obtained from Sigma Chemical Company, St. Louis, Mo.

Animals

Four conditioned mongrel dogs, 2 males and 2 females, weighing 28 to 30 kgs, were studied. Care of the animals were in accordance with the recommendation of the American Association for Accreditation of Laboratory Animals [DHEW(DHHS) publication no. (NIH) 78-23, revised, 1978]. On the day of the experiment, the dogs were fasted overnight. They were anesthetized with phenobarbital (10 mg/kg). They were then intubated orally with a #10 fr. endotracheal tube and ventilated with a Harvard pump ventilator at a rate of 12 breaths per minute and a tidal volume of 15 ml/kg. An arterial line was percutaneously placed in the femoral artery on the day of the experiment.

Physiological measurements

Mean (electronic) and phasic systemic arterial pressures (SAP) were continuously recorded on a Hewlett-Packard recording system (model 7758B) using strain gauge monometers (Hewlett-Packard model 1290A) which were connected to the arterial line. Heart rate was determined from an EKG tracing and continuously recorded on the Hewlett-Packard recording system. Oxyhemoglobin saturation ($SaO_2$) was obtained using a pulse oximeter (BIOX 111, Boulder, Colo.). Continuous time-series records of SAP, HR, and $SaO_2$ were obtained using a Lab Master analog-todigital convertor (16 channel, 12 bit, 30 kHz; Scientific Solutions, Inc.) sampling at 55 Hz and storing the 6 sec averages on a magnetic disk.

$N^G$-monomethylarginine (NMA) was found to reverse the hypotension associated with the administration of TNF. The pressor effect of NMA occurred rapidly (within 2 minutes) and could be antagonized by administration of an excess of L-arginine. The antagonism of the NMA pressor effect was stereospecific for the L-form of arginine.

Figure 7:
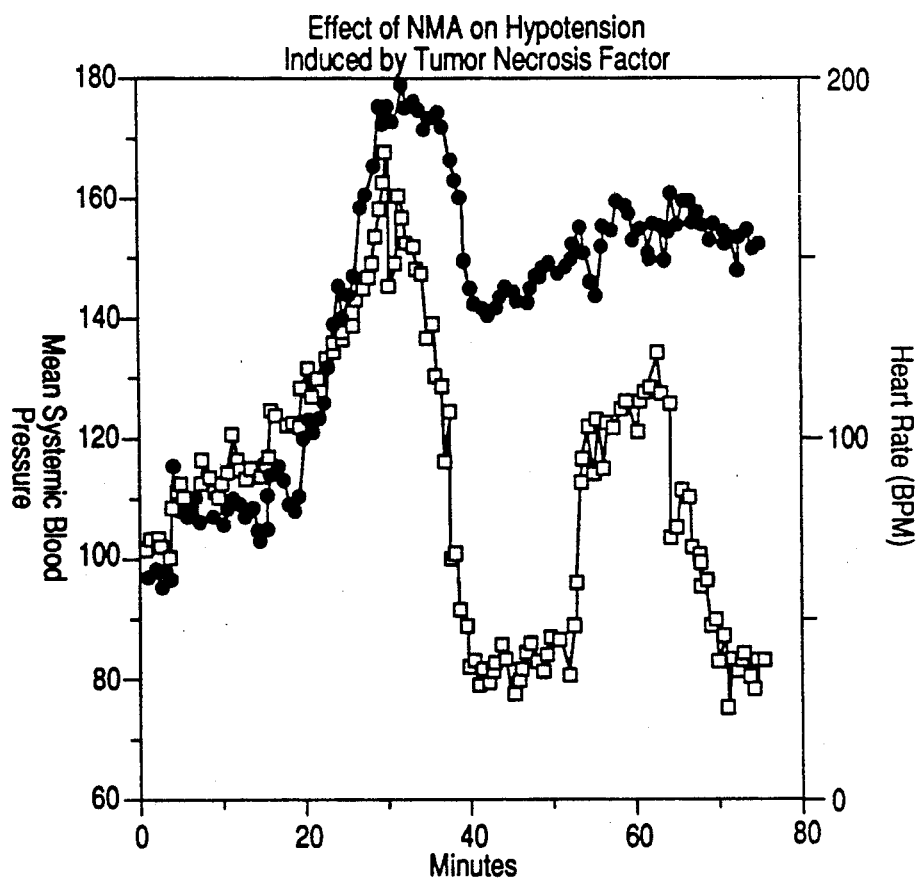
FIG. 7 illustrates variations in canine systemic blood pressure and heart rate as a function of time after TNF, $N^G$methyl L-arginine; and L-arginine administration.
Figure 8A:
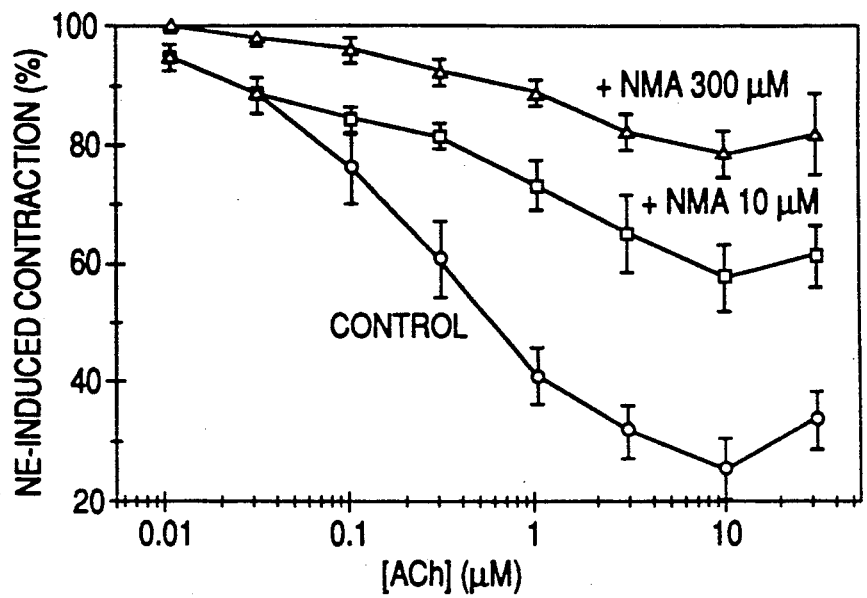
FIG. 8 demonstrates endothelium dependent relaxation of guinea pig pulmonary artery rings in response to acetylcholine, leukotriene D4 and histamine as blocked by L-NMA.
Figure 8B:
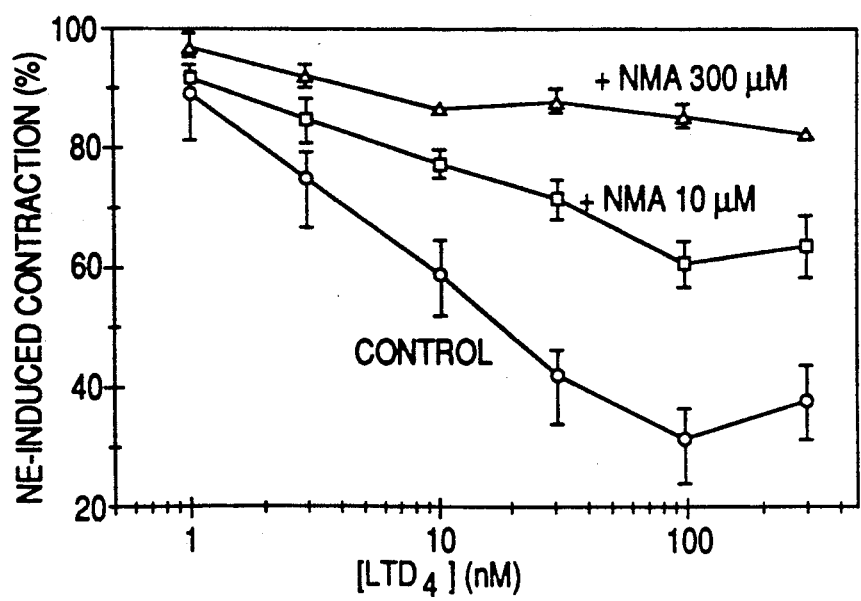
Figure 8C:
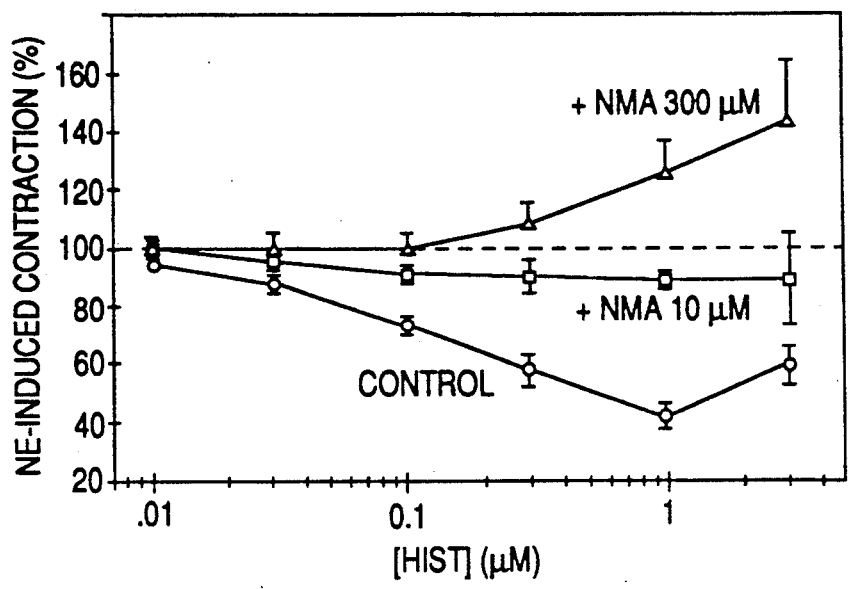
Figure 8D:
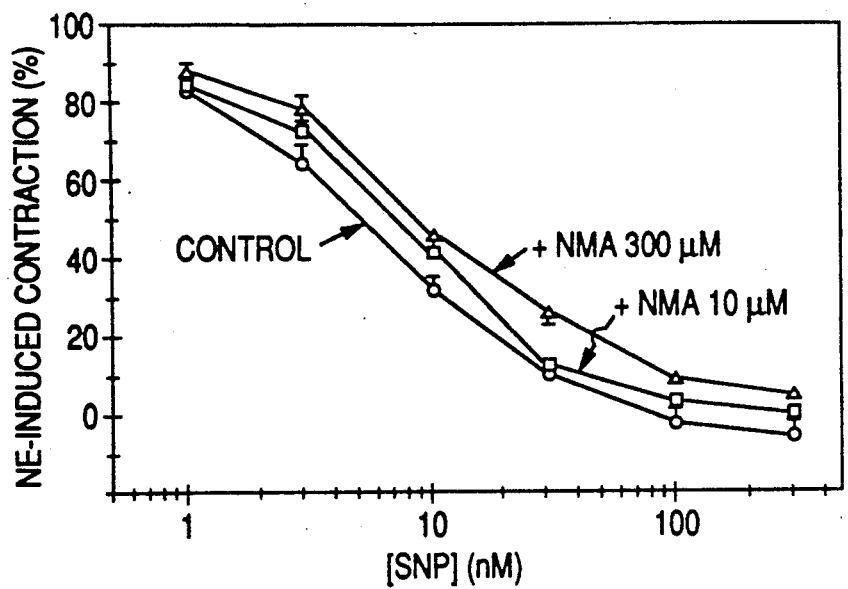
Figure 10A:
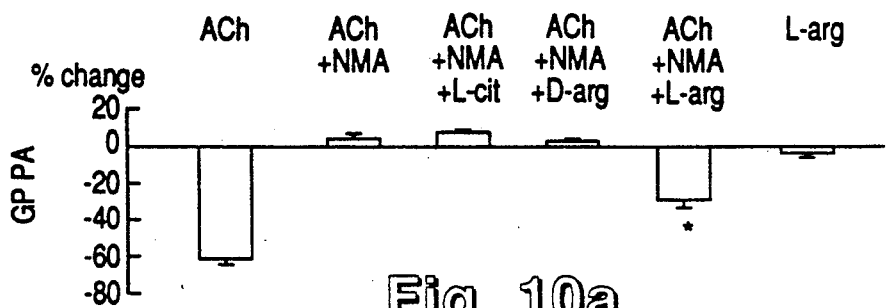
FIG. 10 shows the modification of acetylcholine-induced relaxation by L-$N^G$methylarginine (NMA), L-citrulline, D-arginine and L-arginine in vascular rings from various species.
Figure 10B:
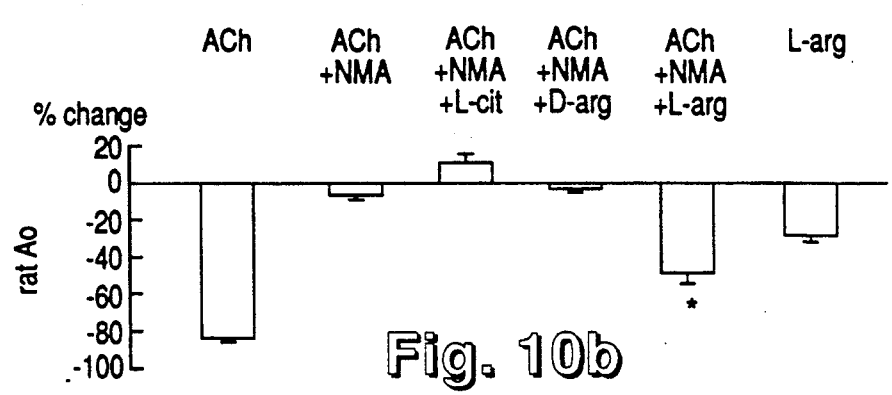
Figure 10C:
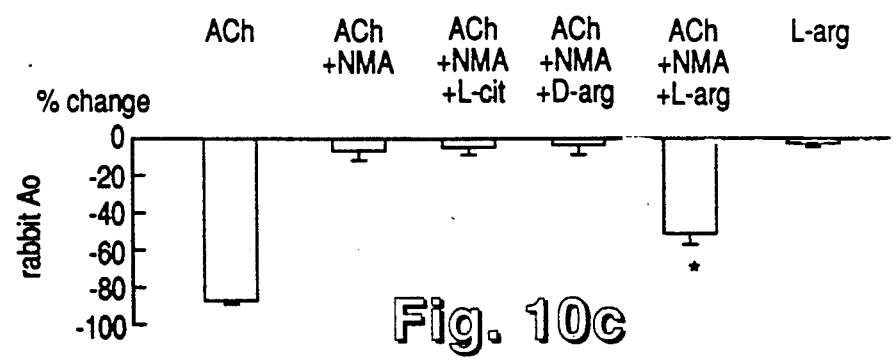
Figure 10D:
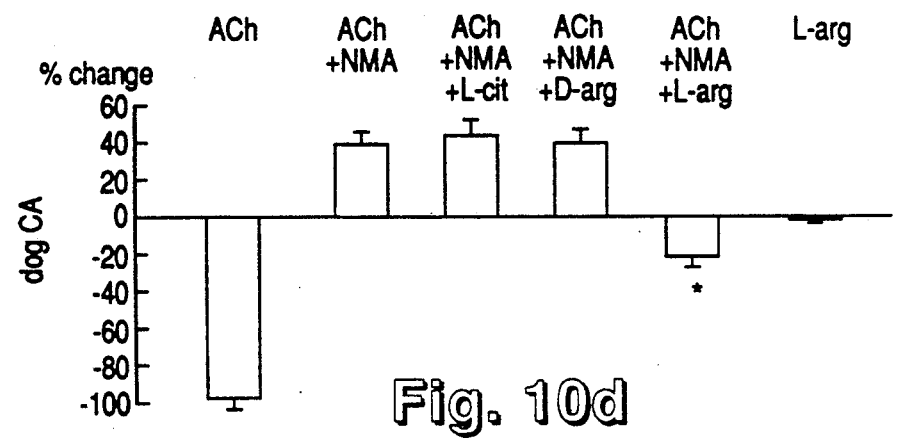
Figure 10E:
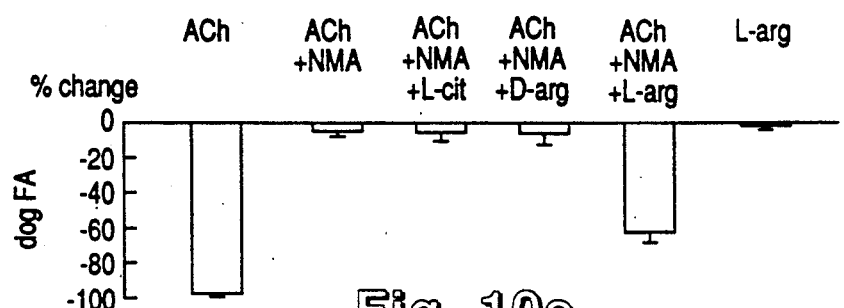

The data shown in FIG. 7 is representative of several animal experiments. There were some variations noted in the degree of hypotension as well as the time of onset of hypotension after TNF administration. Ten ug TNF/kg body weight was intravenously administered at the ten minute timepoint; 4.4 mg $N^G$methyl L-arginine/kg at about 52 minutes; and 3 g L-arginine at about 63 minutes. The onset of hypotension was found to occur between 30 to 60 minutes after TNF. In dog number 3, the SAP dropped rapidly from 106 to 36. The administration of NMA resulted in the rapid increase in blood pressure to an SAP of 116. The response of the remaining two dogs to TNF was similar to that described in FIG. 7.

The administration of NMA (L-$N^G$methylarginine) alone to untreated dogs (n=3) was also tested. Within 1.7 minutes after NMA, the blood pressure initially increased. This was followed by a compensatory decrease in the heart rate with a return of the blood pressure to baseline. The NMA-induced bradycardia lasted 31 minutes. This response was not observed in animals which had been previously treated with TNF.

The administration of L-arginine to NMA-treated dogs resulted in the rapid decrease of blood pressure. Blood pressure was not affected by the administration of L-arginine alone.

The dose-limiting toxicity of tumor necrosis factor administered to patients is hypotension. These experiments imply that nitric oxide, also known as endothelial-derived relaxing factor (EDRF), is the mediator of the hypotension. Furthermore, these hemodynamic changes can be antagonized by an $N^G$-substituted arginine derivative and subsequently restored by the addition of excess arginine, supporting a role for arginine as the substrate for nitric oxide synthesis. The present inventors have shown that $N^G$monomethylarginine can increase the resting blood pressure in the guinea pig. Therefore, nitric oxide may play a role in normal arterial pressure homeostasis. This also appears to be true in the dog.

The pressor response to NMA is much more dramatic in dogs with TNF-induced hypotension than in normotensive dogs. This suggests that tumor necrosis factor (TNF) induced hypotension is due to an excess production of a vasoactive factor (i.e., nitric oxide) which acts to regulate normal resting blood pressure.

Tumor necrosis factor is also involved in the development of the toxicity observed in septic shock. Septic shock is caused by endotoxin, a component of the cell wall of gram negative organisms. The administration of anti-TNF antibodies after TNF exposure does not protect against hypotension. This implies that TNF induces another mediator of hypotension. The results presented here imply that nitric oxide is the true mediator of that response.

EXAMPLE 3

L-$N^G$-substituted arginine analogs block nitric oxide (NO) synthesis from arginine. L-$N^G$-methylarginine (L-NMA) blocks endothelium-dependent relaxation in response to various dilators which act via EDRF/NO release. FIG. 8 shows concentration-response curves for relaxation of guinea pig pulmonary artery rings by endothelium-dependent and endothelium-independent vasodilators and the effect of L-$N^G$-methylarginine (NMA). Vascular rings were preconstricted with 1 uM norepinephrine and relaxation was elicited by cumulative addition of acetylcholine (ACh, panel A), leukotriene D4 (LTD4, panel B), histamine (HIST, panel C) or sodium nitroprusside (SNP, panel D), alone (control), and in the presence of NMA. Points are mean values±SEM (n=4–8).

NMA blocks the action of ACh, LTD4 and HIST, agents which vasodilate by eliciting release of endothelium-derived relaxing factor (EDRF), whereas NMA does not inhibit vasodilatation by SNP (which acts directly on vascular smooth muscle). Thus, NMA has a specific action on EDRF-mediated vasodilatation. It is noteworthy that L-arginine restored relaxation in the presence of L-NMA and that the D-stereoisomer was not an inhibitor of EDRF/NO synthesis.

In this preparation of guinea pig pulmonary artery, arginine analogs with substitutions other than methyl, also served as inhibitors of EDRF/NO synthesis. Those tested include: $NO_2$—, $NH_2$—, $CH_3CH_2$—, $CH_3CH_2CH_2$ and dimethyl (dose-response curves for some of these are shown in FIG. 9). FIG. 9 shows concentration-response curves for inhibition of acetylcholine-induced relaxation of guinea pig pulmonary artery rings by L-$N^G$-substituted arginine analogs. Rings were precontracted with 1 uM norepinephrine, then relaxed by cumulative addition of acetylcholine, alone (control), and then in the presence of various concentrations of arginine analogs. The % inhibition of relaxation is calculated from the maximum ACh-induced relaxation observed in the presence of the arginine analog relative to that in its absence. Points represent mean values±SEM (n=4–6). Of compounds tested thus far, the $NH_2$-substituted derivative appeared to have greatest activity. Substitution of methyl groups on both of the two equivalent guanido nitrogens of arginine results in little or no activity as an inhibitor of EDRF/NO synthesis.

Figure 11A:
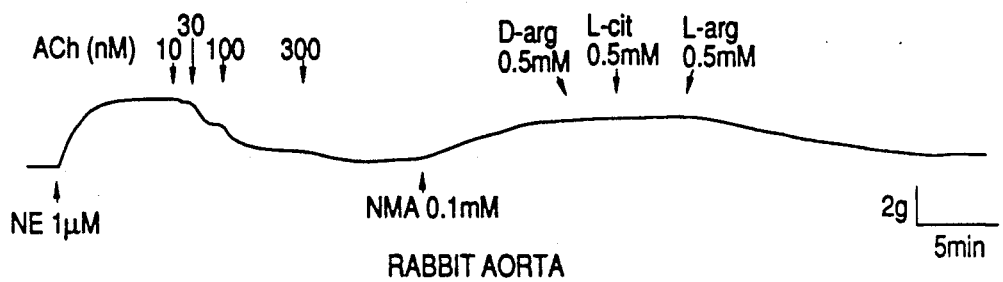
FIG. 11 depicts acetylcholine-induced relaxation and norepinephrine-preconstricted rabbit aorta and human internal mammary artery as modified by L-NMA, D-arginine (D-arg), L-citrulline (L-cit) and L-arginine (L-arg).
Figure 11B:
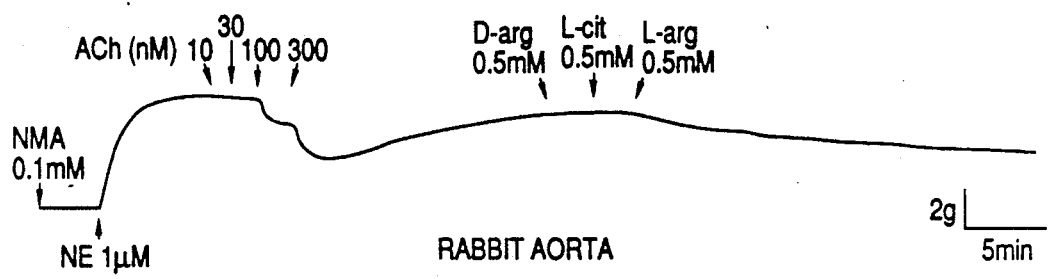
Figure 11C:
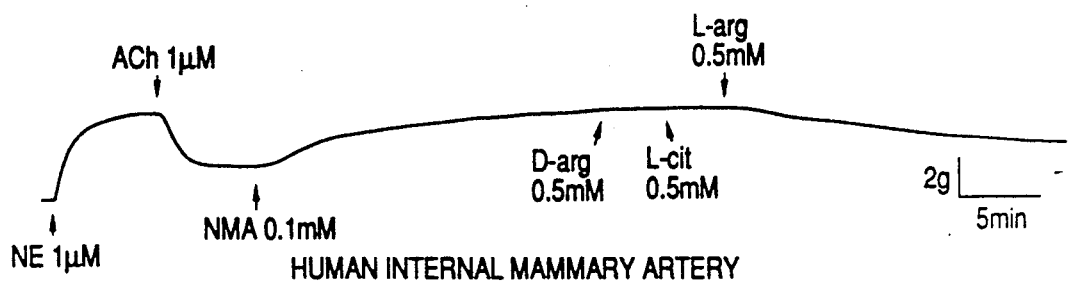

L-NMA was found to act as an arginine reversible inhibitor of EDRF/NO in vascular preparations from an array of species including guinea pig, rat, rabbit, dog and most notably human (see FIGS. 10 and 11). FIG. 10 shows inhibition of acetylcholine (ACh)-induced relaxation by L-$N^G$-methylarginine (NMA) in arteries from various vascular beds and species and the stereospecific reversal by L-arginine. Guinea pig pulmonary artery (GP PA), rat and rabbit aorta (Ao), and dog coronary (CA) and femoral artery (FA) were precontracted with norepinephrine (1 uM) and relaxed with a single concentration of ACh. Concentration of ACh: GP PA 1 uM, rat Ao 0.3 uM, rabbit Ao 0.3, dog CA 0.3 uM and dog PA 0.1 uM. The concentration of NMA was 100 uM except for the rat Ao which was 5 uM. The concentrations of L-citrulline (L-cit), D-arginine (D-arg) and L-arginine (L-arg) were all 0.5 mM. Bars are mean values±SEM (n=4–6).

FIG. 11 contains representative physiograph tracings which depict acetylcholine (ACh)-induced relaxation of norepinephrine (NE)-preconstricted rings prepared from rabbit aorta (upper panel) and human internal mammary artery (lower panel). In both tissues, L-NMA is shown to attenuate ACh-induced vasorelaxation; addition of excess L-arginine restores relaxation.

L-NMA also inhibits EDRF/NO release from bovine endothelial cells grown in culture (FIG. 12) and from the isolated guinea pig heart (FIG. 13) when challenged with an endothelium-dependent vasodilator.

Figure 12:
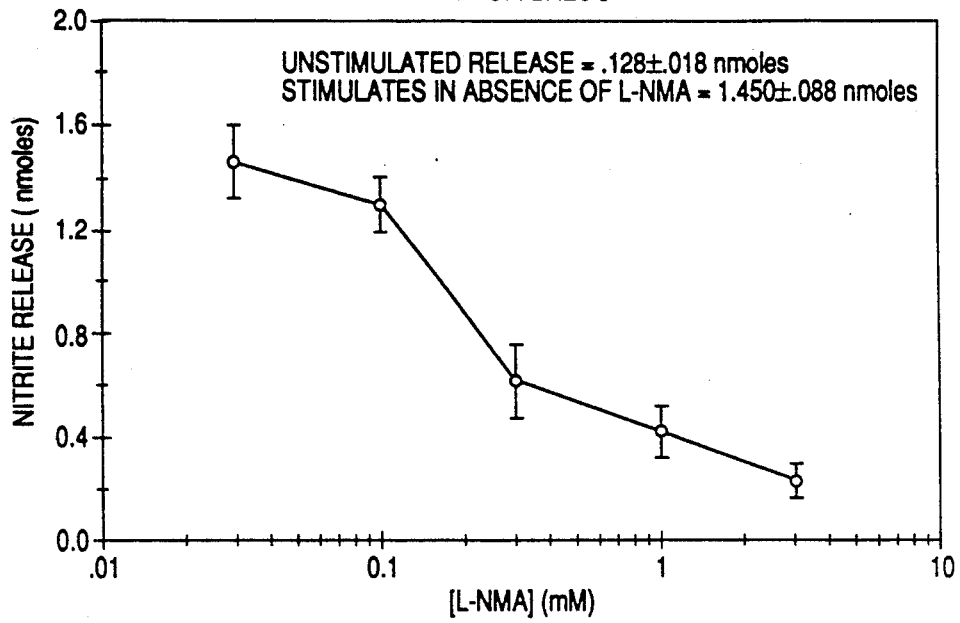
FIG. 12 shows the inhibition by L-NMA of calcium ionophore induced nitrite released from bovine aortic endothelial cells (BAECs).

FIG. 12 illustrates inhibition by L-$N^G$-methylarginine (L-NMA) of calcium ionophore stimulated nitrite release from bovine aortic endothelial cells grown in cell culture. Cells were stimulated to release nitric oxide by addition of 3 ug/ml of ionophore (A23187) to the culture medium, alone, and in the presence of various concentrations of L-NMA. The cumulative release of nitrite (the stable oxidation product of nitric oxide) during a 4-hour incubation at 37° is depicted as a function of L-NMA concentration. Points are mean values±SEM (n=3).

Figure 13:
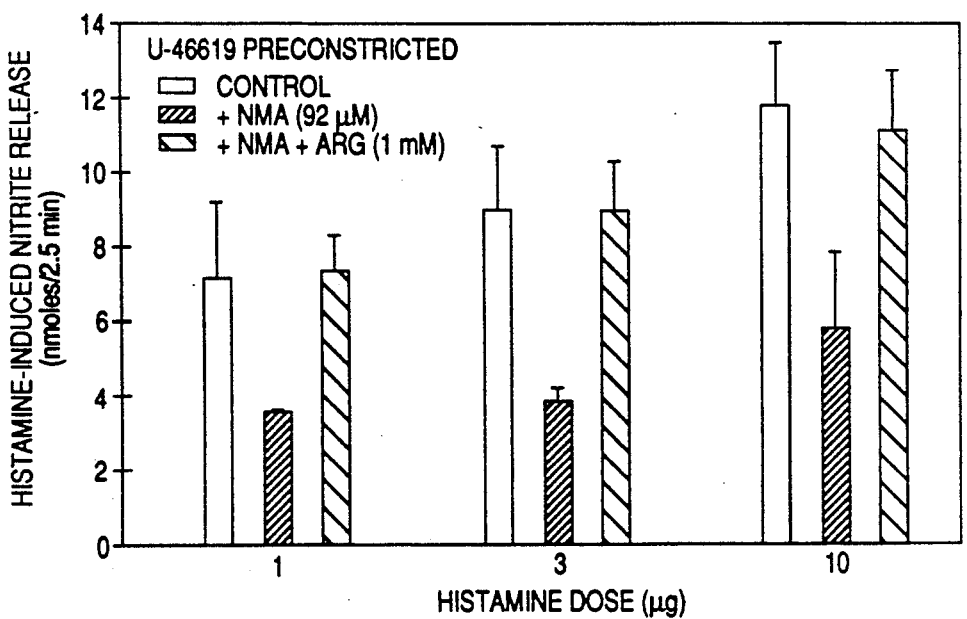
FIG. 13 shows histamine-induced nitrite release from cavian heart: blockade by L-,$N^G$-methylarginine and restoration by L-arginine.

FIG. 13 depicts inhibition by L-$N^G$-methylarginine (NMA) of histamine-induced nitrite release from the isolated coronary perfused guinea pig heart and its restoration by L-arginine. Hearts were perfused at constant pressure (40 cm $H_2O$) with Krebs-Henseleit buffer containing the thromboxane A2 analog (U-46619, 86 nM) to induce coronary vasoconstriction. Histamine was administered as a rapid bolus injection into the aorta and net nitrite release during the subsequent 2.5 minutes was determined. Bars represent mean values±SEM (n=4–6). Not shown here is that histamine elicits a dose-dependent increase in coronary flow (vasodilation) which is attenuated by L-NMA, but restored by addition of excess L-arginine. Thus, it appears that nitric oxide synthesis from L-arginine mediates, at least in part, histamine-induced coronary artery vasodilatation in the guinea pig heart.

Figure 14:
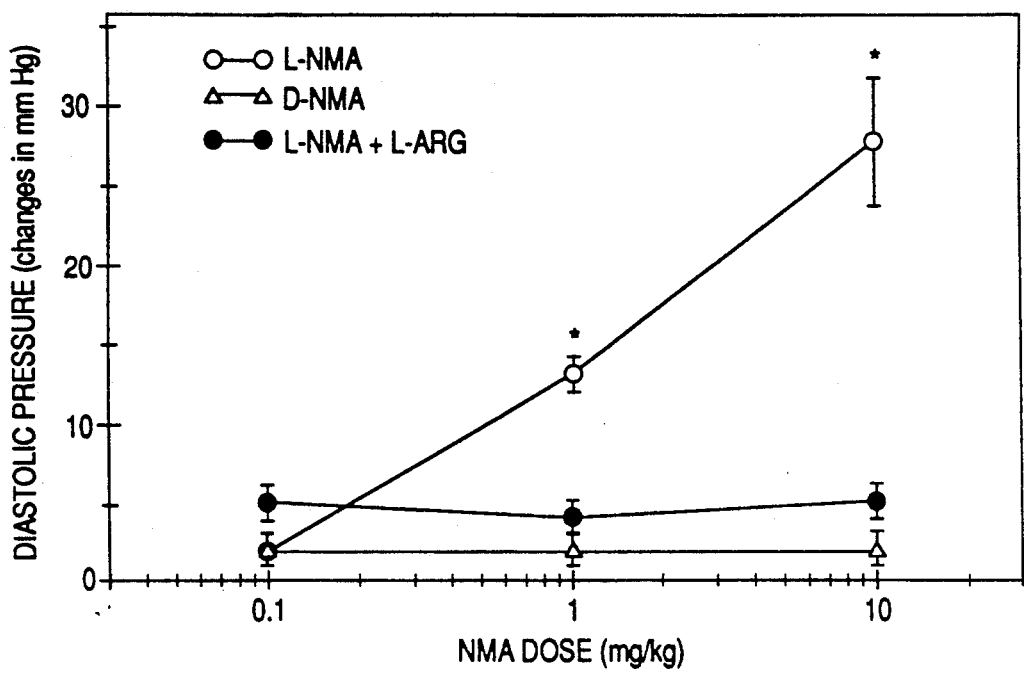
FIG. 14 shows the dose-response relationship for the pressor effect of NG-methylarginine in the anesthetized guinea pig.
Figure 15:
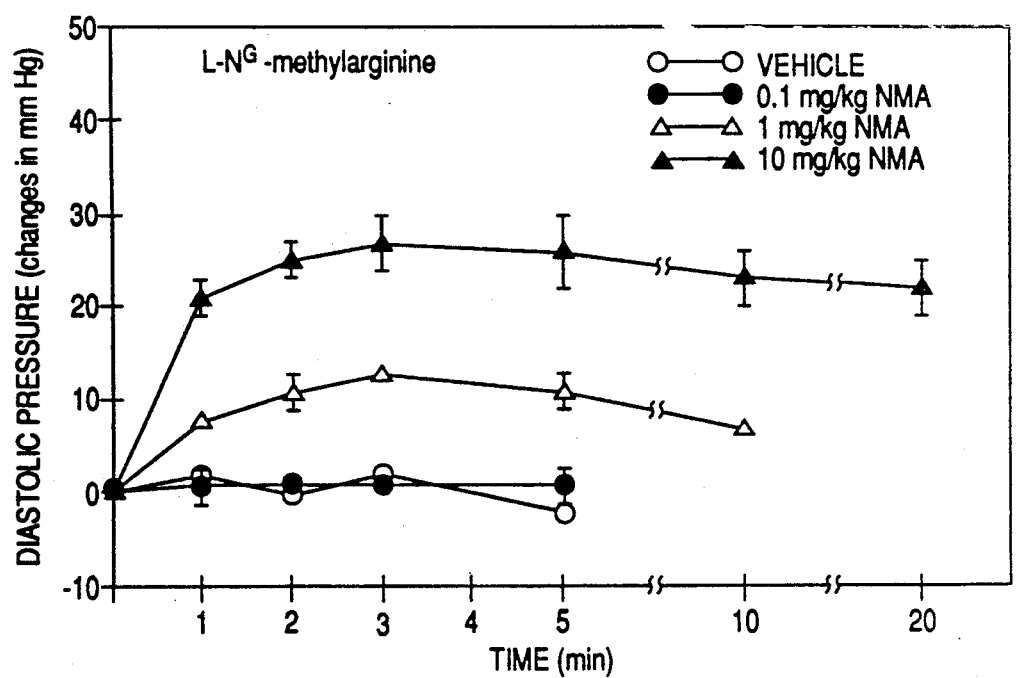
FIG. 15 shows the time course and dose-dependence of L-$N^G$methylarginine-induced hypertension in the guinea pig.
Figure 16:
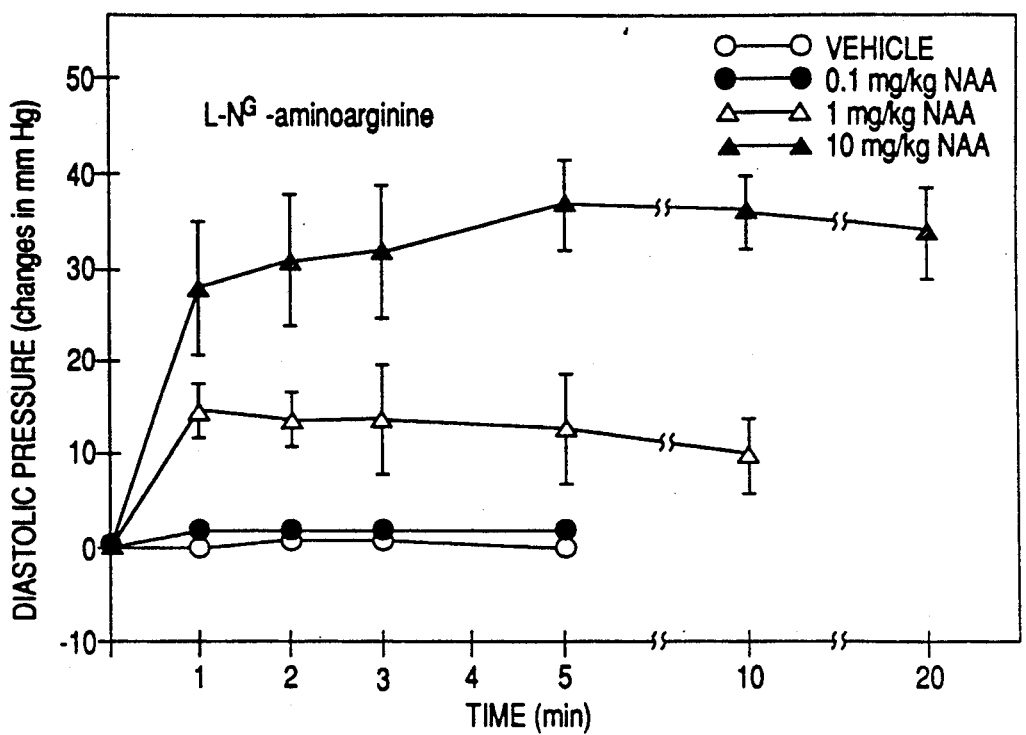
FIG. 16 shows the time course and dose-dependence of L-$N^G$-aminoarginine-induced hypertension in the guinea pig.
Figure 17:
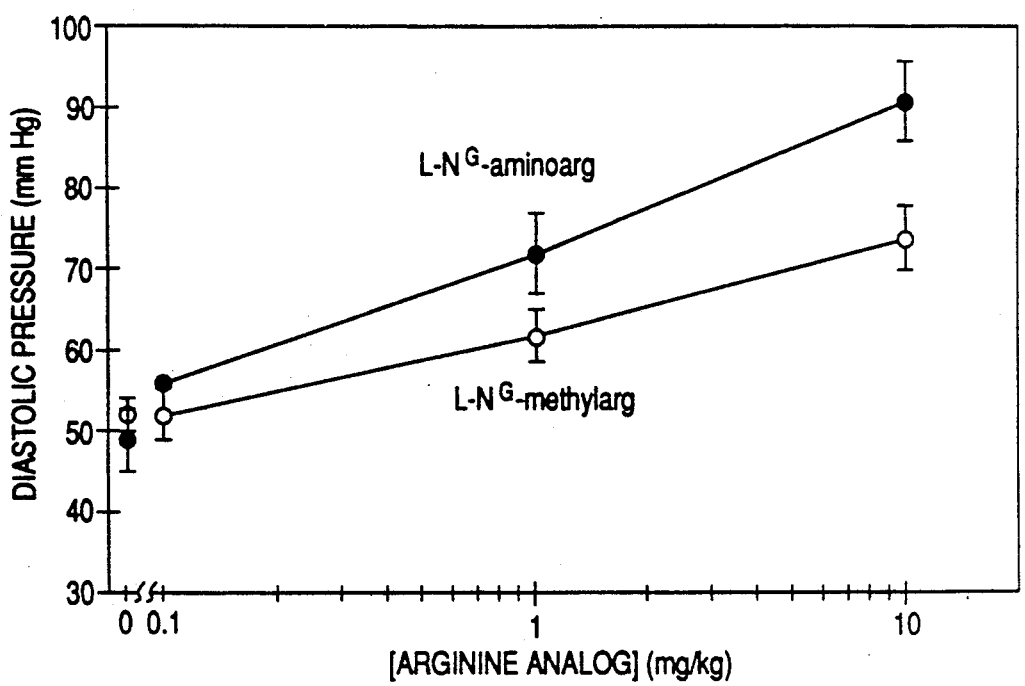
FIG. 17 shows the pressor effects of L-$N^G$-aminoarginine and L-$N^G$-methylarginine as a function of concentration in the guinea pig.

Administration of L-NMA (1–10 mg/kg, intravenously) but not D-NMA to an anesthetized guinea pig elicits a sustained rise in diastolic blood pressure due to inhibition of resting levels of EDRF/NO synthesis (FIGS. 14 and 15). A similar but more potent action was observed with L-$N^G$-aminoarginine (FIGS. 16 and 17). FIGS. 15 and 16 depict the time course of pressor effect elicited by L-$N^G$-methylarginine (NMA; FIG. 15) and L-$N^G$-aminoarginine (NAA; FIG. 16) in the phenobarbital anesthetized guinea pig. Points are mean changes in diastolic arterial pressure (±SEM; n=4–5). Control systolic and diastolic blood pressure was 75±3 and 51±3 mm Hg, respectively. Similarly L-$N^G$ethylarginine was tested in vivo and found also to cause a sustained pressor effect in the guinea pig.

A murine cancer cell line, EMT6, has been observed to release large quantities of nitrite into the culture medium when activated by bacterial endotoxin, gamma-interferon and various cytokines. Thus EMT6 cytosolic preparations (i.e., cell-free solutions) were prepared and an enzyme activity was characterized which forms NO and citrulline from arginine. This reaction requires NADPH (FIG. 18 and 19) and other cofactors.

Figure 18:
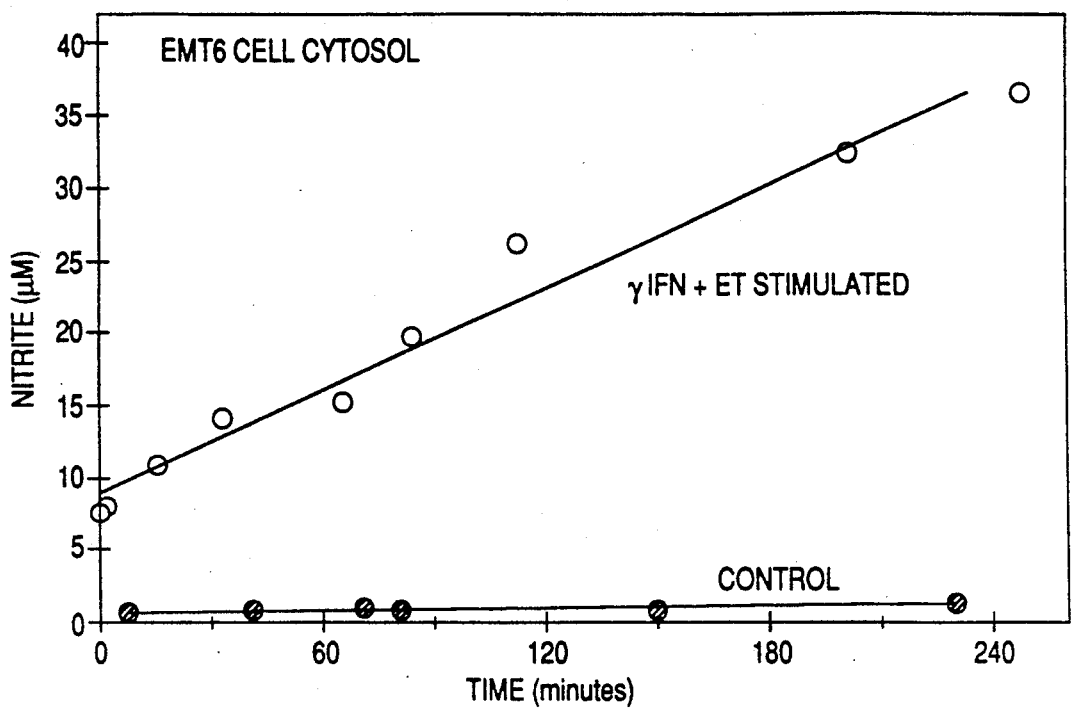
FIG. 18 shows the effect of gamma-interferon and endotoxin stimulation of EMT6 cells on nitrite production by cytosol prepared from these cells.
Figure 19:
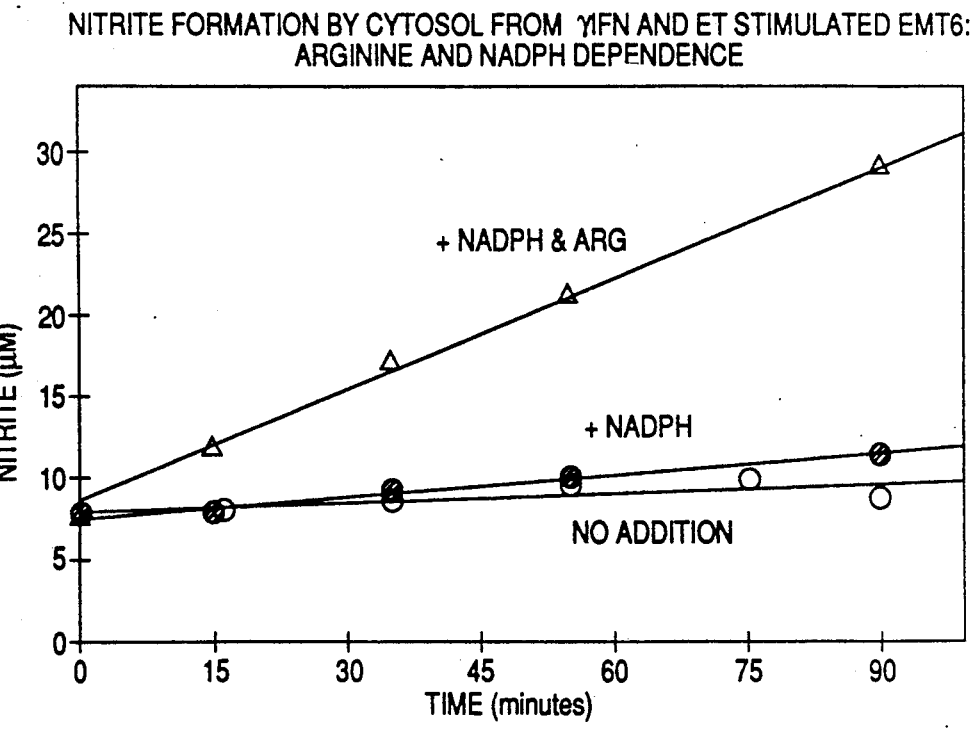
FIG. 19 shows that nitrite formation by the cytosol of EMT6 cells stimulated by gamma-interferon and endotoxin is dependent upon arginine and NADPH.

FIG. 18 shows the time course of nitrite production at 37° C. by cytosolic preparations from EMT6 cells that were either untreated (control) or stimulated with gamma-interferon and endotoxin. Incubation mixtures were 100 ul total volume containing: 40 ul cytosol (100,000×g supernatant), 2 mM L-arginine, 2 mM NADPH, 20 mM TRIS (pH 8.0) and a "cocktail" of protease inhibitors. Nitrite synthesis is observed with cytosol prepared from stimulated cells but not from control cells.

Figure 20:
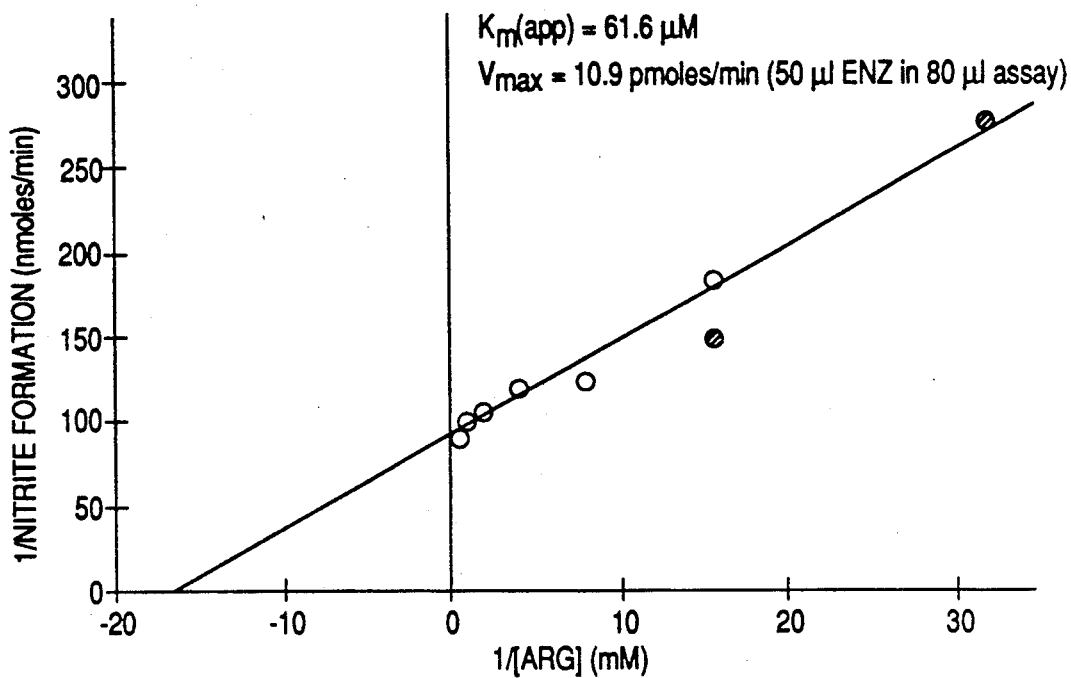
FIG. 20 is a Lineweaver-Burke plot for L-arginine-dependent nitrite synthesis by an enzyme activity present in stimulated EMT6 cytosol (stimulated with gamma-interferon and endotoxin).
Figure 21:
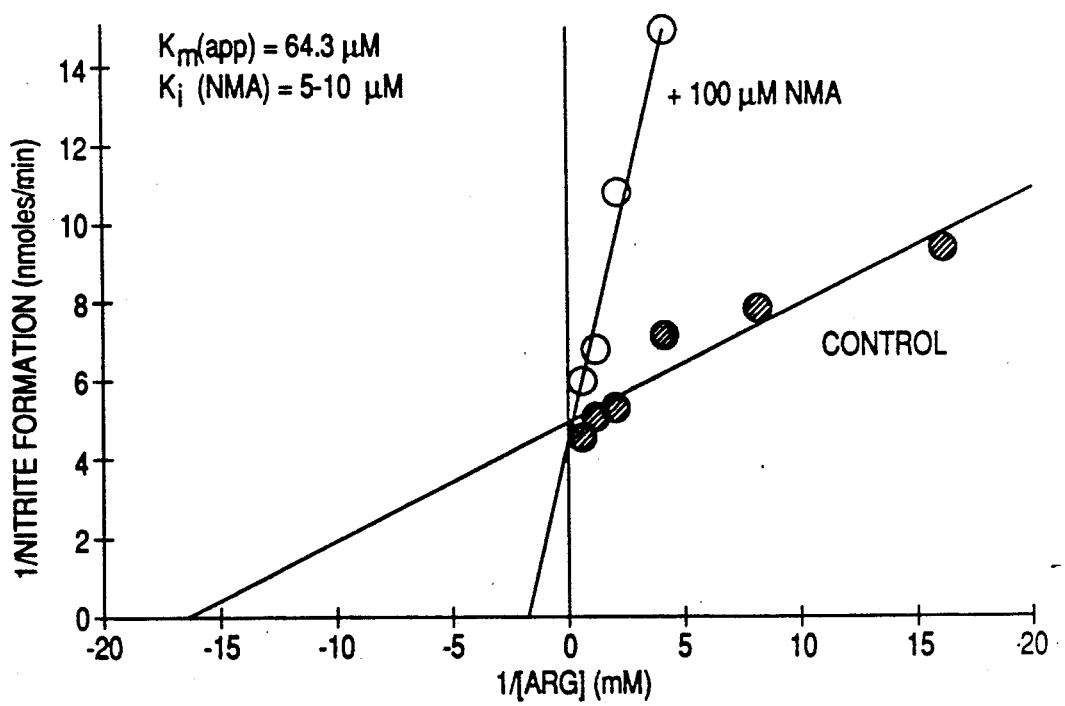
FIG. 21 shows that L-NMA is a competitive inhibitor of the enzyme described in FIG. 20.
Figure 22:
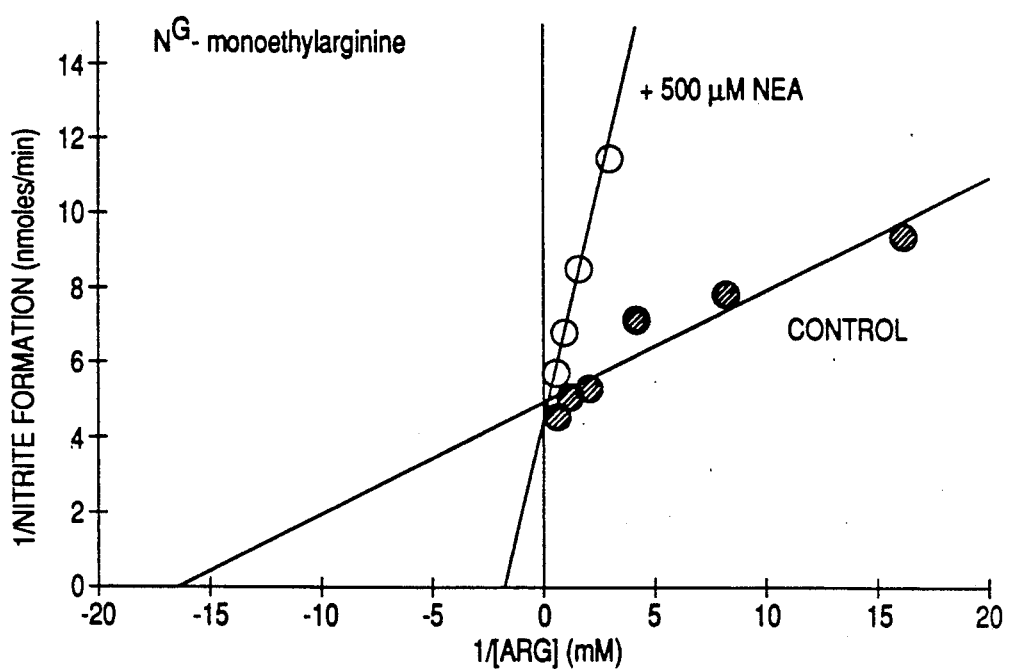
FIG. 22 shows a Lineweaver-Burke plot indicating that NG-monoethylarginine (L-NEA) is a competitive inhibitor of the enzymic activity shown in FIG. 20.

From kinetic studies an apparent Michaelis-Menton constant for L-arginine utilization by the enzyme was deduced. FIG. 20 is a Lineweaver-Burke plot for synthesis of nitrite from L-arginine by cytosol from stimulated EMT6 cells. The rate of nitrite formation was evaluated over a range of ARG concentrations (from 0.03–2.0 mM) under conditions similar to that described for FIG. 18, except that incubates contained 50 ul cytosol in a total volume of 80 ul. Open and filled circles represent results obtained with each of two cytosol preparations. From these results an apparent Km value of 61.6 uM can be extrapolated for the utilization of ARG by the enzyme pathway which forms nitric oxide. $N^G$-substituted arginine analogs were screened for precise quantitation of their ability to inhibit arginine-dependent NO formation by the EMT6 enzyme system. Thus, from data such as that presented in FIG. 21 it can be calculated that L-NMA is a competitive inhibitor of arginine utilization with an apparent Ki or 5–10 uM. The ethyl-substituted compound is approximately 10-fold less active (FIG. 22).

It was concluded from these studies that nitric oxide synthesis from L-arginine is demonstrable in a wide variety of in vitro preparations, from an array of species. Nitric oxide is an important mediator of vasodilation in vivo and probably plays an important role in vascular homeostasis. Finally, $N^G$-substituted arginine analogs may be used as specific blockers of the enzymatic pathway for nitric oxide generation. Thus, this class of arginine antagonists may offer specific relief from hypotension resulting from conditions which cause excess nitric oxide generation, such as those indicated in Examples 1 and 2.

Changes may be made in the arginine antagonists and analogs or method steps of the invention without departing from the scope and spirit of the following claims.

What is claimed is:

1. A method for prophylaxis or treatment of an animal for systemic hypotension induced by gamma-interferon, tumor necrosis factor, interleukin-1 or interleukin-2 said method involving intravascularly administering a therapeutically effective amount of an $N^G$-substituted arginine or an $N^G,N^G$-disubstituted arginine to an animal possibly developing or having such induced systemic hypotension wherein the $N^G$-substituted or $N^G,N^G$-disubstituted arginine has a nitro, amino, lower alkyl, lower hydroxyalkyl or lower alkenyl substituent replacing a hydrogen of a guanidino amino group.

2. A method for prophylaxis or treatment of systemic hypotension in a patient induced by chemotherapeutic treatment with tumor necrosis factor or interleukin-2, said method involving intravascularly administering to said patient a therapeutically effective amount of $N^G$-substituted arginine or an $N^G,N^G$-disubstituted arginine to a patient wherein the $N^G$-substituted or $N^G,N^G$-disubstituted arginine has a nitro, amino, alkyl, hydroxyalkyl, or alkenyl substituent replacing a hydrogen of a guanidino amino group.

3. A method for treatment of an animal for systemic hypotension induced by exposure to endotoxin, said method involving intravascularly administering to said animal a therapeutically effective amount of $N^G$-substituted arginine or $N^G,N^G$-disubstituted arginine to an animal having such induced systemic hypotension, wherein the $N^G$-substituted or $N^G,N^G$-disubstituted arginine has a nitro, amino, lower alkyl, lower hydroxyalkyl, or lower alkenyl substituent replacing a hydrogen of a guanidino amino group.

4. The method of claim 1, 2, or 3 wherein the $N^G$-substituted arginine is a lower $N^G$-aminoarginine, $N^G$-nitroarginine, $N^G$-methylarginine, $N^G$-ethylarginine, or $N^G$-propylarginine.

5. The method of claim 1, 2 or 3 wherein the $N^G$ substituted arginine is $N^G$alkyl arginine.

6. The method of claim 1, 2 or 3 wherein the $N^G$-substituted arginine is $N^G$-substituted L-arginine and the $N^G,N^G$-disubstituted arginine is $N^G,N^G$-disubstituted L-arginine.

7. The method of claim 1, 2 or 3 wherein said therapeutically effective amount of substituted or disubstituted arginine inhibits production in the animal or patient of nitric oxide from arginine.

8. A method for prophylaxis or treatment of an animal for systemic hypotension caused by induced production of nitric oxide, said method involving administering a therapeutically effective amount of an arginine antagonist inhibiting production of said nitric oxide from arginine, to an animal possibly developing or having systemic hypotension.

9. A method for prophylaxis or treatment of an animal for systemic hypotension caused by nitric oxide production induced by gamma-interferon, tumor necrosis factor, interleukin-1, or interleukin-2, said method involving intravascularly administering a therapeutically effective amount of an arginine antagonist inhibiting production of nitric oxide from arginine, to an animal possibly developing or having such systemic hypotension.

10. A method for treatment of an animal for systemic hypotension caused by nitric oxide production induced by exposure to endotoxin, said method involving intravascularly administering a therapeutically effective amount of an arginine antagonist inhibiting production of said nitric oxide from arginine, to an animal having such systemic hypotension.

11. A method for prophylaxis or treatment of an animal for systemic hypotension induced by gamma-interferon, tumor necrosis factor, interleukin-1 or interleukin-2, said method involving intravascularly administering a therapeutically effective amount of lower $N^G$-alkylarginine lower $N^G,N^G$-dialkylarginine, $N^G$-aminoarginine or $N^G$-nitroarginine to an animal possibly developing or having such induced systemic hypotension.

12. The method of claim 11 wherein the $N^G$-alkylarginine or $N^G,N^G$-dialkylarginine has an alkyl substituent selected from the group consisting of methyl, ethyl, and propyl.

13. A method for prophylaxis or treatment of an animal for systemic hypotension induced by gamma-interferon, tumor necrosis factor, interleukin-1, or interleukin-2, said method involving intravascularly administering a therapeutically effective amount of $N^G$-substituted arginine or a $N^G,N^G$-disubstituted arginine wherein the $N^G$-substituted arginine or $N^G,N^G$-disubstituted arginine has a lower hydroxyalkyl, a lower carboxyalkyl or a lower aminoalkyl substituent replacing a hydrogen of a guanidino amino group.

14. A method for treatment of an animal for systemic hypotension induced by exposure to endotoxin, said method involving administering a therapeutically effective amount of lower $N^G$-alkylarginine lower $N^G,N^G$-dialkylarginine, $N^G$-aminoarginine or $N^G$-nitroarginine to an animal having such induced systemic hypotension.

15. A method for prophylaxis or treatment of systemic hypotension in a patient undergoing anticancer chemotherapy with tumor necrosis factor or interleukin-2, said method involving intravascularly administering a therapeutically effective amount of lower $N^G$-alkyl-arginine, $N^G,N^G$-dialkylarginine, lower $N^G$-aminoarginine or $N^G$-nitroarginine to said patient having or possible developing systemic hypotension induced by such chemotherapy.

16. A method for prophylaxis or treatment of a patient for systemic hypotension caused by induced production of nitric oxide, said method involving intravascularly administering a therapeutically effective amount of an arginine antagonist inhibiting production of said nitric oxide from arginine, to a patient possibly developing or having such systemic hypotension.

17. A method for prophylaxis or treatment of a patient for systemic hypotension induced by therapy with tumor necrosis factor, gamma interferon, interleukin-1, or interleukin-2, said method involving intravascularly administering a therapeutically effective amount of lower $N^G$-alkylarginine lower $N^G,N^G$-dialkylarginine, $N^G$-aminoarginine or $N^G$-nitroarginine to a patient possibly developing or having such induced systemic hypotension.

18. A method for treatment of a patient for systemic hypotension induced by exposure to endotoxin, said method involving intravascularly administering a therapeutically effective amount of lower $N^G$-alkylarginine, lower $N^G,N^G$-dialkylarginine, $N^G$-aminoarginine or $N^G$-nitroarginine to a patient having such systemic hypotension.

19. A method for prophylaxis or treatment of a patient for systemic hypotension caused by tumor necrosis factor, gamma-interferon, interleukin-1, or interleukin-2, and resultant production of nitric oxide, said method involving intravascularly administering a therapeutically effective amount of lower $N^G$-alkylarginine, lower $N^G,N^G$-dialkylarginine, $N^G$-aminoarginine or $N^G$-nitroarginine to a patient possibly developing or having such systemic hypotension.

20. A method for treatment of a patient for systemic hypotension caused by exposure of said patient to endotoxin, and resultant production of nitric oxide, said method involving intravascularly administering a therapeutically effective amount of lower $N^G$-alkylarginine, lower $N^GN^G$-dialkylarginine, $N^G$-aminoarginine or $N^G$-nitroarginine to a patient having such systemic hypotension.

21. A method for prophylaxis or treatment of a patient for systemic hypotension caused by nitric oxide production induced by tumor necrosis factor, gamma-interferon, interleukin-1, or interleukin-2, said method involving intravascularly administering a therapeutically effective amount of an arginine antagonist inhibiting production of said nitric oxide from arginine, to a patient possibly developing or having systemic hypotension.

22. A method for treatment of a patient for systemic hypotension caused by nitric oxide production induced by exposure to endotoxin, said method involving intravascularly administering a therapeutically effective amount of an arginine antagonist inhibiting production of said nitric oxide from arginine, to a patient having such systemic hypotension.

23. A method for prophylaxis or treatment of a patient for systemic hypotension caused by nitric oxide production induced by therapy with tumor necrosis factor, said method involving intravascularly administering a therapeutically effective amount of an arginine antagonist inhibiting production of said nitric oxide from arginine, to a patient possibly developing or having systemic hypotension.

24. A method for prophylaxis or treatment of a patient for systemic hypotension caused by nitric oxide production induced by gamma-interferon, tumor necrosis factor, interleukin-1, or interleukin-2, said method involving intravascularly administering a therapeutically effective amount of an arginine antagonist inhibiting production of said nitric oxide from arginine, to an animal possibly developing or having such systemic hypotension, said arginine antagonist being arginine with an $N^G$ substituent selected from the group consisting of amino, nitro, lower alkyl, lower hydroxyalkyl, or lower alkenyl.

25. A method for treatment of an animal for systemic hypotension caused by nitric oxide production induced by exposure to endotoxin, said method involving intravascularly administering a therapeutically effective amount of an arginine antagonist inhibiting production of said nitric oxide from arginine, to an animal having such systemic hypotension, said arginine antagonist being arginine with an $N^G$ substituent selected from the group consisting of amino, nitro, lower alkyl, lower hydroxyalkyl, or lower alkenyl.

26. The method of claim 1, 2, 3, 8, 10, 11, 19 or 25 wherein the therapeutically effective amount is an amount sufficient to inhibit production of nitric oxide from arginine.

27. A method for prophylaxis or treatment of an animal for systemic hypotension induced by gamma-interferon, tumor necrosis factor, interleukin-1 or interleukin-2 said method involving intravascularly administering a therapeutically effective amount of $N^G$-methylarginine or $N^G,N^G$-dimethylarginine to an animal possibly developing or having such induced systemic hypotension.

28. A method for prophylaxis or treatment of an animal for systemic hypotension caused by a production of nitric oxide induced by therapy with gamma-interferon, tumor necrosis factor, interleukin-1 or interleukin-2, said method involving intravascularly administering a therapeutically effective amount of $N^G$-methylarginine or $N^G,N^G$-dimethyl-arginine to an animal possibly developing or having such systemic hypotension.

29. A method for prophylaxis or treatment of an animal for systemic hypotension induced by therapy with gamma-interferon, tumor necrosis factor, interleukin-1, or interleukin-2, said method involving intravascularly administering a therapeutically effective amount of $N^G$-methylarginine or $N^G,N^G$-dimethylarginine to an animal possibly developing or having such induced systemic hypotension.

30. A method for treatment of an animal for systemic hypotension induced by exposure to endotoxin, said method involving intravascularly administering a therapeutically effective amount of $N^G$-methylarginine or $N^G$, $N^G$-dimethylarginine to an animal having such induced systemic hypotension.

31. A method for prophylaxis or treatment of an animal for systemic hypotension caused by production of nitric oxide induced by therapy of said animal with gamma-interferon, tumor necrosis factor, interleukin-1, or interleukin-2, said method involving intravascularly administering a therapeutically effective amount of $N^G$-methylarginine or $N^G,N^G$-dimethylarginine to an animal possibly developing or having such systemic hypotension, said therapeutically effective amount reducing or preventing production of said nitric oxide.

32. A method for treating of an animal for systemic hypotension caused by production of nitric oxide induced by exposure of said animal to endotoxin, said method involving intravascularly administering a therapeutically effective amount of $N^G$-methylarginine or $N^GN^G$dimethylarginine to an animal having such systemic hypotension, said therapeutically effective amount reducing or preventing production of said nitric oxide.

33. The method of any of claims 27–32 wherein the therapeutically effective amount is between about 0.1 mg/kg and about 100 mg/kg.

34. The method of any of claims 27–32 wherein the $N^G$-methylarginine or $N^G,N^G$-dimethylarginine are $N^G$-methyl L-arginine or $N^G,N^G$-dimethyl L-arginine.

35. A method for prophylaxis or treatment of systemic hypotension in a patient induced by chemotherapeutic treatment with tumor necrosis factor or interleukin-2, said method involving administering to said patient a therapeutically effective amount of $N^G$-substituted arginine or an $N^G,N^G$-disubstituted arginine to a patient wherein the $N^G$-substituted or $N^G,N^G$-disubstituted arginine has a nitro, amino, lower alkyl, lower hydroxyalkyl or lower alkenyl substituent, replacing a hydrogen or a guanidino amino group.

36. A method for treatment of an animal for systemic hypotension induced by exposure to endotoxin, said method involving administering to said animal a therapeutically effective amount of $N^G$-substituted arginine or $N^G, N^G$-disubstituted arginine to an animal having such induced systemic hypotension wherein the $N^G$-substituted or $N^G,N^G$-disubstituted arginine has a nitro, amino, lower alkyl, lower hydroxyalkyl, or lower alkenyl substituent replacing a hydrogen of a guanidino amino group.

37. A method for prophylaxis or treatment of an animal for systemic hypotension caused by nitric oxide production induced by therapy with gamma-interferon, tumor necrosis factor, interleukin-1, or interleukin-2, said method involving administering a therapeutically effective amount of an arginine antagonist inhibiting production of said nitric oxide from arginine, to an animal possibly developing or having such systemic hypotension.

38. A method for treatment of an animal for systemic hypotension caused by nitric oxide production induced by exposure to endotoxin, said method involving administering a therapeutically effective amount of an arginine antagonist inhibiting production of said nitric oxide from arginine, to an animal having such systemic hypotension.

39. A method for prophylaxis or treatment of an animal for systemic hypotension induced by therapy with gamma-interferon, tumor necrosis factor, interleukin-1 or interleukin-2, said method involving administering a therapeutically effective amount of lower $N^G$-alkylarginine lower or $N^G, N^G$-dialkylarginine to an animal possibly developing or having such induced systemic hypotension.

40. The method of claim 35, 36, 37 or 38 wherein the administering is parenteral.

41. The method of claim 40 wherein the administering is intraperitoneal.

42. The method of claim 35, 36, 37 or 38 wherein the administering is enteral.

43. The method of claim 35, 36, 37 or 38 wherein the administering is topical, intradermal or intramuscular.

* * * * *

UNITED STATES PATENT AND TRADEMARK OFFICE
CERTIFICATE OF CORRECTION

PATENT NO. : 5,028,627

DATED : July 2, 1991

INVENTOR(S) : Robert G. Kilbourn, Steven Gross, Roberto Levi, Owen W. Griffith

It is certified that error appears in the above—identified patent and that said Letters Patent is hereby corrected as shown below:

In claim 15, column 12, line 60 immediately after the term 'alkyl-arginine,' insert the term --lower--.

In claim 15, column 12, line 60, immediately after the term '$N^G,N^G$- dialkylarginine' delete the word "lower".

In claim 15, column 12, line 62, delete the word "possible" and insert the word --possibly-- therefor.

In claim 32, column 14, line 60, delete the word "treating" and insert the word --treatment-- therefor.

In claim 35, column 15, line 16, delete the word "or" and insert the word --of-- therefor.

In claim 39, column 16, line 18, delete the phrase "lower or" and insert the phrase --or lower-- therefor.

Signed and Sealed this

Second Day of March, 1993

Attest:

STEPHEN G. KUNIN

*Attesting Officer*  *Acting Commissioner of Patents and Trademarks*